(12) United States Patent
Saxena et al.

(10) Patent No.: US 7,005,298 B1
(45) Date of Patent: Feb. 28, 2006

(54) MICROPROPAGATION AND PRODUCTION OF PHYTOPHARMACEUTICAL PLANTS

(75) Inventors: Praveen K. Saxena, Guelph (CA); Susan J. Murch, Cambridge (CA); Sankaran Krishnaraj, Guelph (CA); Tannis Y. Slimmon, Guelph (CA)

(73) Assignee: University of Guelph, (CA)

( * ) Notice: Subject to any disclaimer, the term of this patent is extended or adjusted under 35 U.S.C. 154(b) by 0 days.

(21) Appl. No.: 09/937,452

(22) PCT Filed: Mar. 24, 2000

(86) PCT No.: PCT/CA00/00305

§ 371 (c)(1),
(2), (4) Date: Nov. 28, 2001

(87) PCT Pub. No.: WO00/57690

PCT Pub. Date: Oct. 5, 2000

Related U.S. Application Data

(60) Provisional application No. 60/151,045, filed on Aug. 27, 1999.

(51) Int. Cl.
*C12N 5/00* (2006.01)
*C12N 5/02* (2006.01)
*C12N 1/20* (2006.01)

(52) U.S. Cl. .................................. 435/420; 435/800
(58) Field of Classification Search ................ 435/420, 435/800
See application file for complete search history.

(56) References Cited

U.S. PATENT DOCUMENTS 5,869,340 A    2/1999    Shetty

OTHER PUBLICATIONS

Hypericum Perforatum In vitro culture and the production of Hypericin and other secondary Metabolites Cellarove et al.*
Experiments in Plant Tissue Culture. Third Edition. John H. Dodds. Lorin W. Roberts.*
Stojakowska, Anna; "Production of parthenolide in organ cultures of feverfew"; XP-000937973; *Plant CH Tissue and Organ Culture,* vol. 47, 1997, pp. 159-162.
Banerjee, Suchitra; "In vitro multiplication of *Centella asiatica*, a medicinal herb from leaf explants"; XP-000937832; vol. 76, No. 2; Jan. 1999; pp. 147-148.
Brutovska et al.; "Cytogenetic variablility of in vitro regenerated *Hypericum perforatum* L. plants and their seed progenies"; *Plant Science,*; XP000938218; pp 221-229.
Database Biosis Online; Norton; "In-vitro propagation of Ericaceae; a comparison of the activity of cytokinins . . . "; XP-002148178; Scientia & Horiculturae, vol. 27, pp 335-340 (abstract).
Database Biosis Online; Cocker et al.; "In vitro culture of *Echinacea purpurea*"; XP-002148179; Phytopatology; vol. 87; (abstract).
Smith, R., "Establishment of Calli and Suspension Cultures", *Methods for Plant Molecular Biology,* Academic Press, Inc., Chap. 22, pp. 343-353 (1988).
Potrykus, I. et al., "Protoplasts: Isolation, Culture, Plant Regeneration", *Methods for Plant Molecular Biology,* Academic Press, Inc., Chap. 23, pp. 355-383 (1988).
Power, J. et al., "Fusion and Transformation of Plant Protoplasts", *Methods for Plant Molecular Biology,* Academic Press, Inc., Chap. 24, pp. 385-401 (1988).

\* cited by examiner

*Primary Examiner*—Annette H. Para
(74) *Attorney, Agent, or Firm*—Merchant & Gould P.C.

(57) ABSTRACT

The development of an in vitro regeneration system that utilizes a plant growth regulator having cytokinin activity for the induction of de novo shoots or somatic embryos on explants of phytopharmaceutical plants is provided. Transfer of the regenerated shoots or somatic embryos into a solid or liquid medium with no plant growth regulators results in the rapid and prolific growth of viable plantlets. The method and its modifications are intended for application to all phytopharmaceutical plants, in particular St. John's wort (*Hypericum perforatum* cv. Anthos), Huang-qin (*Scutellaria baicalensis*), *Echinacea* sp., Feverfew (*Tanacetum parthenium*), garlic (*Allium* sp.) and the like. Furthermore, a process for the uptake of nutrients, minerals or additives from the growth medium and accumulation of these in the consumable biomass of plants, hereafter referred to as phytofortification, is also described. This process provides additives within a bioavailable form within plants and renders nutrients and additives amenable for easy assimilation by the human of livestock digestive systems.

23 Claims, 12 Drawing Sheets

MICROPROPAGATION AND PRODUCTION OF PHYTOPHARMACEUTICAL PLANTS

CROSS REFERENCE TO RELATED APPLICATION

This application claims priority from PCT International Application Number PCT/CA00/00305, filed Mar. 24, 2000, which claims priority from Canadian Patent Application No. 2,267,012, filed Mar. 25, 1999 and is a Provisional Application No. 60/151,045, filed Aug. 27, 1999, which applications are incorporated herein by reference.

FIELD OF THE INVENTION

The present invention relates to a method for the micropropagation of phytopharmaceutical plants. Furthermore, the present invention relates to a method for the fortification of phytopharmaceutical plants with nutrients, minerals or other compounds, and to plants obtained using this method.

BACKGROUND OF THE INVENTION

Medicinal plants play an important role in health care throughout the world —especially in non-industrialized continents such as Africa, South America and parts of Asia. Even in many industrialized countries, a number of traditional plants are widely used by a majority of people for minor to moderate everyday ailments through self-medication.

Although many traditional medicinal plant remedies do not undergo extensive scientific testing, they are very popular and their sale is not restricted by government regulatory agencies. Some medicinal plants do have substantial laboratory and clinical testing and those that fall into this category are referred to as phytopharmaceuticals.

One of the major problems associated with phytopharmaceutical plant preparations is the variability in the content of the medicinally active ingredients. This problem was highlighted in Belgium in 1997, when more than 100 people were diagnosed with total destruction of their kidneys through irreversible interstitial fibrosis caused by a misidentified Chinese medicinal plant (Betz, 1998). This has led to strict government controls on purity and levels of active constituents in phytopharmaceutical products in Europe. Such strict regulation does not currently exist, however, in most countries, including Canada and the United States.

The variability in medicinal content of phytopharmaceutical plants is likely the result of a variety of factors including: year-to-year and plant-to-plant variability in medicinal content; adulteration of medicinal preparations with misidentified plant species; a lack of adequate methods for production and standardization of the crop; a lack of understanding of the unique plant physiology or efficacy with human consumption; and consumer fraud. In addition, phytopharmaceutical plant preparations are typically produced from field-grown crops and therefore are susceptible to infestation by bacteria, fungi and insects that can alter the medicinal content of the preparations.

Past and current efforts have centered on ensuring that preparations of phytopharmaceutical plants contain the correct plant material, that the plant material is processed according to a standardized protocol and that the finished product contains specific levels of a specific marker compound. Another approach has been the application of traditional pharmaceutical development methods to isolate a single "active" component and to synthesize versions of the so-called "drug". This process usually involves the dissection of the plant into chemical components and attempts to identify a single compound responsible for the induction of the desired effects in mammals. Most phytopharmaceutical plant preparations are formulated from whole plants and contain a variety of compounds which may be working synergistically to produce the desired effect. Although Drug Identification Numbers (DIN) have been issued for various preparations on the basis of a standard concentration of a marker compound, there may be no physiological effect in humans which can be directly attributed to this marker compound. The lack of any real knowledge base for the phytopharmaceutical industry has lead to the current situation in which the sale of phytopharmaceutical plant preparations is driven largely by enthusiasm rather than solid scientific research. Therefore, with the currently available methods, there is no way to ensure quality, efficacy or safety of phytopharmaceutical plant preparations.

Deficiency of trace minerals in humans may occur as the result of inadequate intake of the mineral in the diet or decreased or impaired absorption in the presence of adequate dietary intake (Whittaker, 1998). The problem of mineral deficiency is most prevalent in developing countries where there may be a dietary imbalance in the nutrient composition. It is estimated that more than 2 billion people worldwide suffer from mineral deficiencies, exhibited as common ailments and diseases (for example, zinc deficiency may lead to low fertility; iodine deficiency may be expressed as muscle and thyroid-related ailments; vitamin C deficiencies render susceptibility to common viruses and colds). Factors that decrease or impair the absorption of minerals and nutrients include dietary constituents which as phytate or fiber, drugs or other chemicals that can interact with essential trace minerals and interactions between essential nutrients (Whittaker, 1998).

The conventional approaches to overcome these deficiency-related ailments are dietary supplements (e.g. vitamin C tablets, zinc lozenges), and consumption of fortified food (iron fortified baby foods; vitamin D fortified milk; iodized salt). Foods commonly fortified with mineral nutrients include flour, bakery goods, rice, macaroni products, breakfast cereals and infant formula (Whittaker, 1998). The efficacy of fortification of foods with inorganic mineral compounds, for example $Zn(SO_4)_2$, is limited by the low bioavailability of the ions and the high degree of loss through excretion. Recent studies on the bioavailability of fortified nutrients and vitamins in humans have indicated that greater than ⅔ of the nutrients and additives may not be absorbed by the human gastrointestinal system, as they are not in a bioavailable form. In 1993, the Consultant Group on International Agricultural Research (CGIAR) suggested that increasing the mineral uptake of plants could be used to address the problems associated with deficiency of zinc and other nutrients (Ruel and Bouis, 1998).

*Echinacea* products are currently among the best-selling herbal remedies in North America and have been for several years (Schardt, 1998). Preparations of *Echinacea* sp. have historically been used for the treatment of common human ailments such as colds and flu (Kindscher, 1992). Commercially prepared extracts and whole dried tissue preparations are made from the root of *Echinacea* species, a crop which takes about 3 years to produce a saleable product.

Commercial preparations of *Echinacea* are frequently supplemented with inorganic zinc to increase medicinal efficacy. Zinc supplements are recommended for the maintenance of good health, enhanced immune system function, reduced expression of viral symptoms, tissue formation and for the metabolism of proteins, fats and carbohydrates (Gibson et al., 1998). In commercial preparations, zinc is added to the *Echinacea* root material during processing in the inorganic form $Zn(SO_4)_2$. Therefore the absorbance of the supplemented Zn is limited by the low bioavailablity. Researchers have reported that certain amino acids, cysteine-containing peptides and organic acids, released during digestion may enhance zinc absorption, possibly by forming soluble ligands with zinc or by preventing the formation of the insoluble zinc-phytate complex (Gibson et al., 1998).

Zinc deficiency is one of the leading causes of limited growth rate, loss of appetite, skin lesions, delayed wound healing, hypogonadism, delayed sexual maturation and impaired immune responses in mammals (Whittaker, 1998).

The process of controlling zinc status is a tightly regulated balance of absorption and excretion processes. Zinc is more efficiently absorbed in small amounts than at higher concentrations and other dietary factors such as fiber and phytate inhibit zinc absorption. In addition, the practice of fortifying foods with iron may have a negative impact on zinc status (Whittaker, 1998). Therefore, the recommendations of the American Food and Drug Administration encourage the prudent use of nutrients as supplements to foods but does not encourage the fortification of food staples.

Similarly, zinc fortification of animal feeds is monitored under the guidelines of Agriculture and Agri-Food Canada and limited to less than 250 ppm. In the USA, ongoing research has indicated that supplementation of animal feeds with 3000 ppm inorganic zinc results in more rapid muscle and protein accretion and an overall acceleration in the rate of growth.

One of the most popular medicinal plants in North America is St. John's wort (*Hypericum perforatum*). In 1998, 7.5 million Americans used St. John's wort for the treatment of neurological disorders and depression (Greenwald, 1998) based on a demonstrated efficacy in numerous clinical trials (Linde et al., 1996). In 1997, the National Institute of Health, Office of Alternative Medicine invested $4.3 million dollars in a 3-year clinical trial to compare the effects of St. John's wort, a placebo and a standard antidepressive drug in patients suffering from mild depression (NIH, 1997). The standard for St. John's wort preparations is "the whole fresh or dried plant or its components, including not less than 0.04% naphthodianthrones of the hypericin group calculated as hypericin." (St. John's wort Monograph, 1997) but a recent clinical trial demonstrated that the therapeutic effect of St. John's wort was correlated to the concentration of a second compound hyperforin, (Laakmann et al., 1998). Similar to synthetic antidepressants, the activity of hyperforin was found to cause inhibition of uptake of serotonin, dopamine, noradrenaline, GABA and L-glutamate in animal cell cultures (Chatterjee et al., 1998). Further confounding the situation, studies into the unique physiology of St. John's wort have identified more than 25 additional compounds that may have medicinal activity (Miller, 1998; Nahrstedt and Butterweck, 1997; Evans and Morgenstern, 1997) including the recent report of the presence of relatively high levels of the mammalian neurohormone melatonin (Murch et al., 1997). Therefore, it is clear that the neurological efficacy requires whole plant preparations of St. John's wort.

Lithium, is a mineral element also used in the treatment of depression and neurological disorders. Frequently, traditional pharmaceutical antidepressant therapies can be augmented with lithium in those situations where a patient's depression is either treatment-resistant or partially and/or insufficiently responsive to treatment (Schweitzer & Tuckwell, 1998). Lithium treatment has been used for more than 40 years and has been found to be effective in 60–80% of all patients although the mode of action is not clear. Toxicity of lithium salts can occur when the blood lithium becomes elevated as a result of fever, diabetes, weight loss diets, salt restricted diets or diarrhea.

It is important to solve the problem of the variability in the medicinal content of preparations of phytopharmaceutical plants so that they can be used reliably and effectively. One solution to producing a reliable source of phytopharmaceutical plants is the development and application of in vitro micropropagation procedures to these plants. However, to date, there is no known general method for the in vitro micropropagation of phytopharmaceutical plants.

Furthermore, the phytofortification of phytopharmaceutical plants is desired in order to produce plants that comprise desired additives, nutrients and other compounds of interest that are available in a biocompatible form.

There is, therefore, a need within the phytopharmaceutical plant industry for the development of an in vitro system for the reliable and reproducible propagation of phytopharmaceutical plants, and when desired the phytofortification of phytopharmaceutical plants with desired compounds of interest.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a method for the micropropagation of phytopharmaceutical plants. Furthermore, the present invention relates to a method for the fortification of phytopharmaceutical plants with nutrients, minerals or other compounds, and to plants produced using this method.

The present invention provides a method (A) for the in vitro micropropagation of a phytopharmacuetical plant comprising:
  a) culturing a sterile explant of the phytopharmaceutical plant on an induction medium comprising at least one plant growth regulator having cytokinin activity, to form regenerated tissue; and
  b) transferring the regenerated tissue to a basal medium and culturing to form plantlets.

This invention is also directed to the method (A) as defined above wherein the phytopharmaceutical plant is selected from St. John's wort (*Hypericum perforatum* cv. Anthos), Huang-qin (*Scutellaria baicalensis*), *Echinacea* sp., feverfew (*Tanacetum parthenium*) and garlic (*Allium* sp.).

The invention is relates to the method (A) as defined above wherein the plant growth regulator having cytokinin activity may be natural or synthetic and is selected from the group consisting of thidiazuron (TDZ; N-phenyl-N-(1,2,3-thidiazol-yl)urea), benzylaminopurine (BAP), zeatin, CPPU (N-(2-chloro-4pyridyl)-N(-phenyl urea), and 2-i-P (N-6-(2-isopentenyl) adenine or 6-gamma,gamma-dimethylallylamino purine).

In another of its aspects, the present invention also includes a method (B) for the in vitro micropropagation of a phytopharmaceutical plant comprising:
  a) culturing a sterile explant of the phytopharmaceutical plant on an induction medium comprising a suitable concentration of at least one plant growth regulator having cytokinin activity, to form regenerated tissue;

b) transferring the regenerated tissue to a basal medium and subculturing to optimize formation of regenerated tissue; and c) transferring the regenerated tissue to a basal medium and culturing to form plantlets.

This invention is also directed to the method (B) as defined above wherein the phytopharmaceutical plant is selected from St. John's wort (*Hypericum perforatum* cv. Anthos), Huang-qin (*Scutellaria baicalensis*), Echinacea sp., feverfew (*Tanacetum parthenium*) and garlic (*Allium* sp.).

The present invention is also directed to the method (B) as defined above wherein the plant growth regulator having cytokinin activity may be natural or synthetic and is selected from the group consisting of thidiazuron (TDZ; N-phenyl-N'-(1,2,3-thidiazol-yl) urea), benzylaminopurine (BAP), zeatin, CPPU (N-(2-chloro-4pyridyl)-N(-phenyl urea) and 2-i-P (N-6-(2-isopentenyl) adenine or 6-gamma,gamma-dimethylallylamino purine).

In another aspect, the present invention provides a method (C) for fortification of an in vitro grown phytopharmacuetical plant comprising:

a) culturing a sterile seedling, explant or regenerated tissue to form a plantlet; and b) subculturing the plantlet onto a basal medium containing at least one additive of interest and allowing uptake and accumulation of the at least one additive of interest in a bioavailable form within the plantlet.

Preferably, the sterile explant is cultured in step (a) of Method (C) on a medium comprising at least one growth regulator having cytokinin activity under conditions suitable to form regenerated tissue.

In another aspect, the present invention also provides a method (D) for the in vivo fortification of a phytopharmaceutical plant comprising:

a) culturing a plantlet or seedling using mthod (A) as decribed above, under conditions sufficient for clonal micropropagation and growth of the plantlet or seedling; and b) adaptating the plantlet or seedling to a hydroponic environment with a recycling solution containing at least one additive of interest to allow uptake and accumulation of the at least one additive of interest in a bio-available form within plantlet.

The phytopharmaceutical plant used in any one of methods (A), (B), (C) and (D) may be selected from:

Achillea millefolium
Achyranthes bidentata
Aconitum napellus
Adonis aestivalis
Agastache mexicana
Agrimonia eupatoria
Agathosma betulina
Allium sp
Anchusa officinalis
Anemopsis californica
Angelica dahurica
Angelica polymorpha sinensis (*A. sinensis*)
Arnica Montana
Ammi visnaga
Arctostaphylos uva-ursi
Asclepias tuberosa
Astragalus membranaceus
Astragalus chinensis
Baphicacanthus cusia
Bixa orellana
Bupleurum falcatum
Brugmansia (*Datura*) spp.
Campanula rapunculus
Carum roxburgianum
Carum copticum
Cassia tora
Chamaelirium luteum
Chimaphila umbellata
Commiphora africana
Conium maculatum
Crithium maritimum
Datura metel (*Datura alba*)
Datura inoxia
Dracocephalum moldavica
Echinacea sp.
Eclipta alba (*E. prostrata*)
Ephedra nevadensis
Eriodictyon californicum
Eucommia ulmoides
Eupatorium perfoliatum
Filipendula vulgaris (*F. hexapetala*)
Gaultheria procumbens
Geum urbanum
Houttuynia cordata
Hydrocotyle asiatica (*Centella asiatica*)
Hypericum perforatum cv. Anthos
Inula helenium
Jatropha curcas
Leptospermum scoparium
Lespedeza capitata
Ligusticum porteri
Ligustrum lucidum
Lithospermum officinale
Lycium barbarum
Mucuna pruriens
Mandragora officinarum
Origanum dictamnus
Parietaria judaica (*P. officinalis*)
Phyllanthus emblica
Picrasma excelsa
Piniella ternate
Pogostemon patchouli
Polygonum multiflorum
Porophyllum ruderale ssp. *macrocephalum*
Prunella vulgaris
Pueraria lobata (*P. thunbergiana*)
Rauvolfia serpentina
Rivea corymbosa
Sanguinaria Canadensis
Satureja douglasii
Schizonepeta tenuifolia
Scutellaria baicalensis
Solanum xanthocarpum (*S. surattense*)
Sutherlandia frustescens
Tabebuia impetiginosa
Tanacetum parthenium
Tribulus terrestris
Trichosanthes kirilowii
Turnera diffusa
Voacanga africana
Withania somnifera The nutrient used in method (C) or (D) may be selected from, but not limited to, boron, calcium, chloride, chromium, cobalt, copper, iron, lithium, iodine, magnesium, manganese, molybdenum, nickel, phosphorous, potassium, selenium, silicon, sodium, sulphur, tin, vanadium and zinc.

The production of phytopharmaceutical plants in vitro has several advantages:
- plants are grown in sterile, standardized conditions;
- individual superior plants can be identified and clonally produced;
- plant material is consistent and therefore, precise biochemical characterizations can be achieved; and
- eventually, protocols can be developed for the improvement of the crop through genetic manipulation.

This summary of the invention does not necessarily describe all necessary features of the invention but that the invention may also reside in a sub-combination of the described features.

These and other aspects of the present invention will be described in greater detail hereinbelow.

BRIEF DESCRIPTION OF THE DRAWINGS

The features of the present invention will become more apparent from the following description in which reference is made to the appended drawings wherein:

FIG. 2 shows St. John's wort as produced according to the present invention.

FIG. 3 (a) is a histological characterization showing de novo shoot induction of St. John's wort and meristematic zones formed at the hypodermal region of the hypocotyl explant (arrows) at 7 days of culture on TDZ-containing induction medium. (bar=50 $\mu$m).

FIG. 4 shows several aspects of Echinacea as produced according to the method as described herein.

FIG. 5 shows several aspects of Echinacea as produced according to the method of the present invention.

FIG. 6 (a) shows a histological characterization showing a series of anticlinal and periclinal divisions leading to the formation of well defined protoderm regenerated from petiole explants of Echinacea purpurea at 14 days of culturing on induction medium containing BAP. (bar=50 $\mu$m).

DETAILED DESCRIPTION OF THE INVENTION

Figure 1:
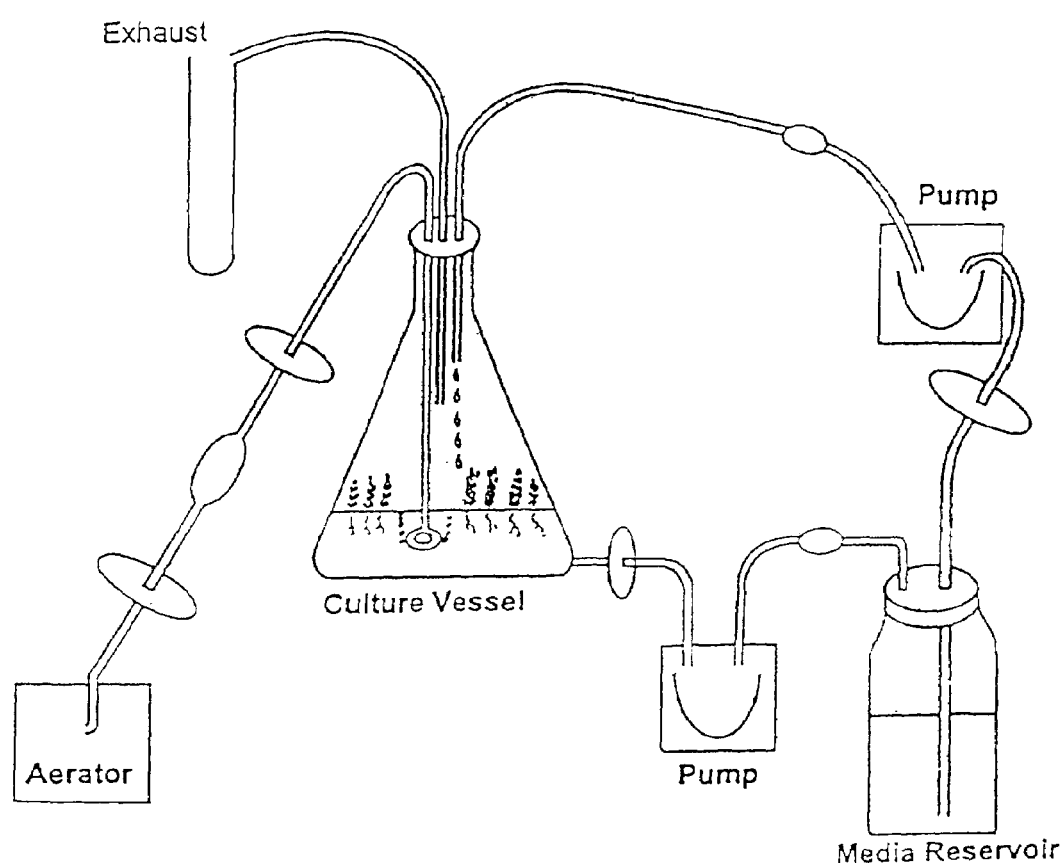
FIG. 1 shows a sketch of a bioreactor system suitable for use with the methods of the invention.

The present invention relates to methods for the micropropagation of phytopharmaceutical plants, and to plants obtained by using this method. Furthermore, the present invention relates to methods for the fortification of phytopharmaceutical plants with nutrients, minerals or other compounds and to plants obtained using these methods.

The following description is of a preferred embodiment by way of example only and without limitation to the combination of features necessary for carrying the invention into effect.

As used herein, the term phytopharmaceutical plant means any plant that exhibits a beneficial or medicinal effect when administered via any means to a human or an animal. The beneficial or medicinal effect of the phytopharmaceutical plant may have been verified by laboratory or clinical study. A phytopharmaceutical plant may also comprises one or more active agents whose identity has been identified. Preferably the phytopharmaceutical plant is a medicinal plant, for example, but not limited to:

Achillea millefolium
Achyranthes bidentata
Aconitum napellus
Adonis aestivalis
Agastache mexicana
Agrimonia eupatoria
Agathosma betulina
Allium sp
Anchusa officinalis
Anemopsis californica
Angelica dahurica
Angelica polymorpha sinensis (A. sinensis)
Arnica Montana
Ammi visnaga
Arctostaphylos uva-ursi
Asclepias tuberosa
Astragalus membranaceus
Astragalus chinensis
Baphicacanthus cusia
Bixa orellana
Bupleurum falcatum
Brugmansia (Datura) spp.
Campanula rapunculus
Carum roxburgianum
Carum copticum
Cassia tora
Chamaelirium luteum
Chimaphila umbellata
Commiphora africana
Conium maculatum
Crithium maritimum
Datura metel (Datura alba)
Datura inoxia
Dracocephalum moldavica
Echinacea sp.
Eclipta alba (E. prostrata)
Ephedra nevadensis
Eriodictyon californicum
Eucommia ulmoides
Eupatorium perfoliatum
Filipendula vulgaris (F. hexapetala)
Gaultheria procumbens
Geum urbanum
Houttuynia cordata
Hydrocotyle asiatica (Centella asiatica)
Hypericum perforatum cv. Anthos
Inula helenium
Jatropha curcas
Leptospermum scoparium
Lespedeza capitata
Ligusticum porteri
Ligustrum lucidum
Lithospermum officinale
Lycium barbarum
Mucuna pruriens
Mandragora officinarum
Origanum dictamnus
Parietaria judaica (P. officinalis)
Phyllanthus emblica
Picrasma excelsa
Piniella temate
Pogostemon patchouli
Polygonum multiflorum
Porophyllum ruderale ssp. macrocephalum
Prunella vulgaris
Pueraria lobata (P. thunbergiana)
Rauvolfia serpentina
Rivea corymbosa
Sanguinaria Canadensis
Satureja douglasii
Schizonepeta tenuifolia
Scutellaria baicalensis
Solanum xanthocarpum (S. surattense)
Sutherlandia frustescens
Tabebuia impetiginosa
Tanacetum parthenium
Tribulus terrestris
Trichosanthes kirilowii
Turnera diffusa
Voacanga africana
Withania somnifera More preferably the plant is selected from the group consisting of St. John's wort (Hypericum perforatum cv. Anthos), Huang-qin (Scutellaria baicalensis), Echinacea sp., feverfew (Tanacetum parthenium), garlic (Allium sp.).

The present invention also pertains to the method of phytofortification. Phytofortification refers to the incorporation of one or more additives of interest within a plant, for example, one of the plants identified above, thereby rendering one or more additives in a bio-available form suitable for human or animal consumption. Preferably, the one or more additives of interest is selected from, but not limited to, an essential nutrient, vitamin, metabolite or combination thereof. Phytofortification utilizes the inherent ability of a plant or plantlet to uptake one or more additives from a growth medium. Plantlets are grown in a controlled environment and accumulate the nutrients in the consumable biomass. The process of phytofortification exploits the natural biological processes that convert inorganic nutrients and other additives into complex organic molecules within the plant tissues. This process renders nutrients and additives amenable for efficient assimilation and increased the efficiency of adsorption by human or livestock digestive tracts through digestion of plant-based macromolecules. The bioavailability of the phytofortified additives and supplements in the plant products facilitates the utilization of the nutrients for nutritional and medicinal processes.

The present invention therefore provides a method for the phytofortification of in vitro or in vivo-grown phytopharmaceutical plants.

The term "additive" includes mineral elements, vitamins, metabolites and other nutrients as are known in the art. Examples of an additive, which are not to be considered limiting in any manner includes the mineral elements, boron, calcium, chloride, chromium, cobalt, copper, iron, lithium, iodine, magnesium, manganese, molybdenum, nickel, phosphorous, potassium, selenium, silicon, sodium, sulphur, tin, vanadium and zinc.

In Vitro Micropropagation

In general terms, one of the methods of this invention involves obtaining a sterile explant of a phytopharmaceutical plant and culturing it on an induction medium comprising a suitable concentration of at least one plant growth regulator that has cytokinin activity for a suitable period of time in order to produce regenerated tissue. The explant can be selected from any part of the plant including seeds, petiole, hypocotyl, cotyledon, stem and leaves. If the tissue is hypocotyl, it is preferably etiolated hypocotyl.

The plant growth regulator having cytokinin activity may be any such synthetic or natural plant growth regulator including for example, but not limited to, thidiazuron (TDZ; N-phenyl-N-(1,2,3-thidiazol-yl)urea), benzylaminopurine (BAP), zeatin, CPPU (N-(2-chloro-4pyridyl)-N(-phenyl urea) and 2-i-P (N-6-(2-isopentenyl) adenine or 6-gamma, gamma-dimethylallylamino purine). Preferably, the plant growth regulator having cytokinin activity is selected from thidiazuron (TDZ) and benzylaminopurine (BAP).

The concentration and duration of exposure of the sterile explant to the plant growth regulator(s) having cytokinin activity may vary depending on the species of the plant. A person skilled in the art can determine the concentration of growth regulator, and the duration of exposure by culturing an explant from the phytopharmaceutical plant at various concentrations of the plant growth regulator(s) and for various exposure times and determining the optimal conditions for the production of the desired amount of regenerated tissue. The regenerated tissue may be in the form of shoots, calli or somatic embryos. Most commonly the regenerated tissue is in the form of shoots. It is desired to use a concentration and duration of exposure of the plant growth regulator(s) having cytokinin activity which minimizes residual effects including a decrease in the number of regenerants, vitrification of the shoots and poor rooting of regenerants.

Following culture of the phytopharmaceutical plant explant on the medium comprising at least one plant growth regulator having cytokinin activity, the explant with regenerated tissue may be transferred to basal medium and cultured under standard conditions, as known to one of skill in the art, to form plantlets. Alternatively, the explant with regenerated tissues may be transferred to basal medium and subcultured for a further period of time to obtained the desired amount of regenerated tissue formed. Following this subculturing, the regenerated tissue may be transferred to either solid or liquid basal medium and cultured under standard conditions to form plantlets.

Examples of the media which may be used for this method, which are to be considered non-limiting, are presented in Table 1:

TABLE 1

|  | Induction Medium | Solid Basal | Liquid Basal |
| --- | --- | --- | --- |
| pH | 5.7 | 5.8 | 5.8 |
| MS salts (Murashige & Skoog, 1962) | + | + | + |
| B5 Vitamins (Gamborg, 1968) | + | + | + |
| Sucrose | 3% | 3% | 3% |
| Gellan Gum | 0.3% | 0.3% | — |
| Growth Regulator | Cytokinin activity | — | — |

Sterile explants of phytopharmaceutical plants may be obtained using standard procedures, for example, but not limited to, seedlings grown from sterile seeds on water agar in darkness in a growth cabinet at a suitable temperature, for example in the range of about 22 to about 28° C., preferably at about 24° C., for a suitable period of time, for example about 10 to about 60 days. Seeds may be sterilized by immersion in alcohol, for example about 70 to about 95% ethanol, for a short period of time, for example 5 seconds to about 5 minutes, followed by soaking in a solution containing about 1 to about 3%, preferably 1.5%, (v/v), sodium hypochlorite (Javex), or other suitable bleach, for a period of time, for example, but not limited to, about 15 to about 25 min, preferably about 17 to about 22 min. The bleach solution preferably also contains from about 1 to about 10 drops of Tween-20 per 100 mL of solution. Following this sterilization procedure the seeds are thoroughly rinsed with sterile deionized or distilled water.

Some seeds from phytopharmaceutical plants are particularly difficult to sterilize due to a high amount of fungal contamination. In these instances a biostatic agent such as plant preservative mixture (PPM) may be added to the water agar during culture. The amount of the biostatic agent to be used can be determined by culturing the seed or explant on water agar with varying amounts of the biostatic agent and determining the lowest concentration that would be biostatic to fungal growth and still allow seed germination or explant regeneration.

An alternate method for the sterilization of explants may involve surface sterilization of field or greenhouse-grown plant material. With this method, tissue is excised from the intact plant and immediately immersed in sterile water. A similar sterilization protocol would then be followed in which the tissue is rinsed with an alcohol, from about 70 to about 90%, for 30 seconds to 5 minutes, followed by immersion in a bleach solution containing from about 1 to about 10 drops of Tween-20 per 100 mL for 15–40 minutes. Preferably the alcohol is ethanol. Following this sterilization protocol, the tissue should be thoroughly rinsed in sterile deionized or distilled water and cultured on induction medium.

In one embodiment of the present invention, there is provided a method for the in vitro micropropagation of St. John's wort. De novo shoot regeneration can be effectively induced by culturing sterile explants of St. John's wort on a medium containing at least one plant growth regulator having cytokinin activity as defined above. Preferably, the plant growth regulator having cytokinin activity is TDZ. The tissue source for this method can be any suitable sterile tissue from St. John's wort, for example, but not limited to, seeds, stems, petioles, hypocotyl, cotyledon and leaves. Preferably the tissue is etiolated hypocotyl. The concentration of plant growth regulator having cytokinin activity may be in the range of from about 0.001–25 $\mu$mol·L$^{-1}$, preferably from about 1.5 to about 20 $\mu$mol·L$^{-1}$, more preferably about 3 to about 15 $\mu$mol·L$^{-1}$, even more preferably about 4 to about 10 $\mu$mol·L$^{-1}$. The explant is exposed to the inducing media comprising the plant growth regulator having cytokinin activity from about 1 to about 15 days, preferably from about 6 to about 12 days, more preferably from about 8 to about 10 days.

Following initial culture on the induction medium, the explants of St. John's wort may optionally be transferred to solid basal medium and subcultured for a further period of time to obtain the maximum amount of regenerated shoots/explant. The period of time for subculture will depend on the number of shoots/explant desired and the size restrictions of the culture flask. Optimally, the explants of St. John's wort may be subcultured for about 1 to about 15 days, preferably from about 5 to about 12 days, more suitably from about 8 to about 10 days. The regenerated shoots may then be transferred into suitable culture medium to allow roots and plantlets to grow. For example, the shoots may be transferred to culture boxes containing solid basal medium or to flasks containing liquid basal medium. At least 90% of the regenerants develop into mature plantlets which are morphologically similar to seed grown plants raised in the greenhouse. Alternatively, the explants and/or regenerated shoots may be transferred directly from induction medium to solid or basal medium and cultured under conditions to form plantlets.

The culturing of St. John's wort hypocotyl segments on medium in the absence of exogenous growth regulators, produced a large number of explants that formed 1 or 2 adventitious roots. This spontaneous root formation is likely indicative of a high level of endogenous auxin in the etiolated hypocotyls. Supplementation of the culture medium optimized with a plant growth regulator having cytokinin activity suppressed this response. Without wishing to be bound by theory, this effect may be a result of an alteration in the auxin-to-cytokinin ratio within the tissues.

Also described herein is a method for the in vitro micropropagation of Echinacea sp., in particular, Echinacea purpurea. Sterile explants of Echinacea can be cultured on induction medium in the presence of at least one plant growth regulator having cytokinin activity as defined above. Preferably, the plant growth regulator having cytokinin activity is selected from TDZ and BAP. The concentration of plant growth regulator having cytokinin activity may be in the range of from about 0.001 to about 25 $\mu mol \cdot L^{-1}$, preferably from about 0.5 to about 20 $\mu mol \cdot L^{-1}$, more preferably about 1 to about 15 $\mu mol \cdot L^{-1}$.

The tissue source for this method can be any suitable sterile tissue from Echinacea, for example but not limited to seeds, stems, petioles, hypocotyl, cotyledon and leaves. Most preferable the tissue is petiole.

The explant is exposed to the inducing media comprising the plant growth regulator having cytokinin activity from about 1 to about 50 days, preferably from about 6 to about 40 days, more preferably from about 10 to about 35 days. If the induction medium also contains an auxin, the time for exposure to the growth regulator may need to be on the higher side of this range, for example up to about 25 to about 40 days.

Histological observations revealed that regeneration in petiole cultures of Echinacea under the conditions used herein occurred primarily as a result of de novo shoot formation from callusing tissue. Other culture conditions may provide regenerated shoots directly. Histological evidence indicates that some somatic embyros were also formed during the culture of Echinacea petiole explants on induction medium containing BAP. These somatic embryos may be transferred to basal medium and cultured under suitable conditions to form plantlets.

Following initial culture on the induction medium, the explants of Echinacea may optionally be transferred to solid basal medium and subcultured for a further period of time to obtain the maximum amount of regenerated tissue/explant. The period of time for subculture will depend on the amount of regenerated tissue/explant desired and the size restrictions of the culture flask. Optimally, the explants of Echinacea may be subcultured for about 1 to about 15 days, prefereably from about 5 to about 12 days, more preferably from about 8 to about 10 days. The regenerated tissue may then be transferred into suitable culture medium to allow roots and plantlets to grow. For example, the shoots or somatic embyros may be transferred to culture boxes containing solid basal medium or to flasks containing liquid basal medium. Under the conditions defined above, about 70% of the regenerants develop into mature plantlets. These plantlets are morphologically similar to seed grown plants raised in the greenhouse. Alternatively, the explants or regenerated tissue may be transferred directly from induction medium to solid or basal medium and cultured under conditions to form plantlets.

Indirect morphogenesis is the formation of callus from explants which subsequently results in shoots or somatic embryogenesis (Sharp 1980). Callus formation and cell enlargement in tissues may be indicative of high endogenous auxins (Skoog & Miller, 1957). While not wishing to be limited by theory, the formation of callus at the cut ends of the petioles on the control plates as well as elongation of the explants appears to indicate high levels of endogenous auxins present in petioles of Echinacea purpurea. In Echinacea petiole cultures, adjacent cells were stimulated to follow different regenerative routes in the presence of the same cytokinin. While not wishing to be bound by theory, these data may indicated that the endogenous metabolites and growth regulators in individual cells may be different, thereby either predetermining or effecfting the fate of the cells during regeneration.

The present invention also provides a method for the in vitro micropropgation of Huang-qin (Scutellaria baicalensis). Sterile explants of Huang qin can be cultured on induction medium in the presence of at least one plant growth regulator having cytokinin activity. Preferably, the plant growth regulator having cytokinin activity is selected from TDZ and BAP. Most preferably, the plant growth regulator having cytokinin activity is TDZ. The concentration of plant growth regulator having cytokinin activity may be in the range of from about 0.001 to about 25 $\mu mol \cdot L^{-1}$, preferably from about 0.05 to about 20 $\mu mol \cdot L^{-1}$, more preferably from about 1.5 to about 20 $\mu mol \cdot L^{-1}$, and most preferably about 2.0 to about 20 $\mu mol \cdot L^{-1}$.

The tissue source for this method can be any suitable sterile tissue from Huang-qin, for example seeds, stems, petioles, hypocotyl, cotyledon and leaves, preferably the tissue is seed, hypocotyl or stem. Most preferably, the tissue is seed.

The explant is exposed to the inducing media comprising the plant growth regulator having cytokinin activity from about 1 to about 30 days, preferably from about 10 to about 25 days, more preferably from about 14 to about 20 days.

Following initial culture on induction medium, the explants of Huang-qin may optionally be transferred to solid basal medium and subcultured for a further period of time to obtain the maximum number of shoots/explant. The period of time for subculture will depend on the number of shoots/explant desired and the size restrictions of the culture flask. Optimally, the explants of Huang-qin may be subcultured for about 1 to about 15 days, preferably from about 5 to about 12 days, more preferably about 8 to about 10 days. The regenerated shoots may then be transferred into suitable culture medium to allow roots and plantlets to grow. For example, the shoots may be transferred to culture boxes containing solid basal medium or to flasks containing liquid basal medium. Under the condictions described herein, about 90% of the regenerants develop into mature plantlets which are morphologically similar to seed grown plants raised in the greenhouse. Alternatively, the explants and/or regenerated shoots may be transferred directly from induction medium to solid or basal medium and cultured under conditions to form plantlets.

It is another embodiment of the present invention to provide a method for the in vitro micropropgation of feverfew (Tanacetum parthenium). Sterile explants of feverfew can be cultured on induction medium in the presence of at least one plant growth regulator having cytokinin activity. Preferably, the plant growth regulator having cytokinin activity is TDZ. The concentration of plant growth regulator having cytokinin activity may be in the range of from about 0.001 to about 25 $\mu mol \cdot L^{-1}$, preferably 0.5 to about 20 $\mu mol \cdot L^{-1}$, more preferably from about 1.5 to about 15 $\mu mol \cdot L^{-1}$, and most more preferably about 2.0 to about 8 $\mu mol \cdot L^{-1}$.

The tissue source for this method can be any suitable sterile tissue from feverfew, for example seeds, stems, petioles, hypocotyl, cotyledon and leaves. The use of leaf, stem, petiole and hypocotyl is prefered.

The explant is exposed to the inducing media comprising the plant growth regulator having cytokinin activity from about 1 to about 50 days, preferably from about 10 to about 40 days, more preferably from about 20 to about 35 days.

Following initial culture on the induction medium, the explants of feverfew may optionally be transferred to solid basal medium and subcultured for a further period of time to obtain the maximum number of shoots/explant. The period of time for subculture will depend on the number of shoots/explant desired and the size restrictions of the culture flask. Optimally, the explants of feverfew may be subcultured for about 1 to about 15 days, preferably about 5 to about 12 days, more preferably about 8 to about 10 days. The regenerated shoots may then be transferred into suitable culture medium to allow roots and plantlets to grow. For example, the shoots may be transferred to culture boxes containing solid basal medium or to flasks containing liquid basal medium. Under these conditions, about 90% of the regenerants develop into mature plantlets which are morphologically similar to seed grown plants raised in the greenhouse. Alternatively, the explants and/or regenerated shoots may be transferred directly from induction medium to solid or basal medium and cultured under conditions to form plantlets.

The methods developed herein for the in vitro micropropagation of phytopharmaceutical plants are ideal for adaptation for use in a bioreactor-type system such as that shown in FIG. 1. The bioreactor is a large scale, sterile vessel for growth of plant cells and intact plants in culture media and in a controlled environment. Usually the growth media is re-circulated through the culture vessel by a series of peristaltic pumps and media is aerated to ensure rapid and prolific growth of the cultured tissue. In this way, the growth of the plants or cell cultures can be maintained within the closed system in perpetuity. The bioreactor system can be optimized to produce intact plantlets for whole plant preparations or the media components can be altered for the efficient production of various secondary metabolites that serve as the active ingredients in the phytopharmaceutical plant. The use of the bioreactor system will provide phytopharmaceutical manufacturers with a year-round supply of high quality, consistent plant material.

Production of Fortified Phytopharmaceutical Plants

In general terms, the method for the production of fortified phytopharmaceutical plants involves obtaining a sterile, rapidly growing plantlet, seedling or explant of a phytopharmaceutical plant and subculturing it on a medium supplemented with a nutrient mineral element. If an explant is used, it may be selected from any regenerating explant or part of the plant including seeds, petiole, hypocotyl, cotyledon, stem, root and leaves. Preferably, the sterile explant is cultured on a medium containing at least one growth regulator having cytokinin activity under conditions suitable to form regenerated tissue as defined above.

The concentration and duration of exposure of the sterile plantlet or culture to the mineral or nutrient element(s) will vary depending on the species of the plant. A person skilled in the art can determine these values by exposing a rapidly growing culture of the phytopharmaceutical plant at various concentrations of mineral or nutrient element(s) and for various exposure times and determining the optimal conditions for the production of the maximum amount of fortified tissue.

Examples of the media which may be used for the method, which are to be considered non-limiting, are presented in Table 1 (above).

Sterile plantlets of phytopharmaceutical plants may be obtained as described above. However, the present invention also includes an alternate method for the fortification of phytopharmaceutical plants involving the subculture of plantlets or greenhouse-grown plant material in a controlled environment nutrient recycling system. With this method, the plantlets would be grown in on a standardized solution supplemented with the nutrient or mineral element.

The methods as described herein can be used for the phytofortification of plant species with any additive of interest, for example, but not limited to zinc. Zinc deficiency is one of the leading causes of limited growth rate, loss of appetite, skin lesions, delayed wound healing, hypogonadism, delayed sexual maturation and impaired immune responses in mammals (Whittaker, 1998). The preparation of a phytofortified product containing bioavailable zinc provides a new class of nutrient supplement for balancing and maintaining optimal nutritional status for both human and livestock applications. It is to be understood that any phytopharmaceutical plant may be phytofortified using the method of the present invention.

In a preferred embodiment, the phytofortification method described herein can be used to supplement zinc within a desired phytopharmaceutical plant, for example, but not limited to *Echinacea*, during the growth process. The zinc can be supplied either in the growth medium of in vitro grown *Echinacea* seedlings or *Echinacea* plants grown in greenhouse hydroponic systems. The maintenance of an optimized level of zinc and minimization of the phytic acid of the plants ensures the high bioavailability of the zinc supplemented *Echinacea* product.

Example 5 described below outlines the phytophortification of *Echinacea* with zinc. The method involves preparing *Echinacea* petiole explants harvested from 1 month-old sterile seedlings on a media supplemented with a cytokinin as described above. Using liquid cultures, *Echinacea* roots, of a size suitable for commercial use were obtained in about 4 months, as compared to roughly 3 years of growth under field conditions in Canada. Supplementation of the liquid culture medium with zinc resulted in the accumulation of the nutrient in *Echinacea* tissues over a period of 3 to 4 weeks.

Phytofortification of plant species with lithium is also described herein. In a preferred embodiment, the method can be used to fortify St. John's wort with lithium, however, other phytopharmaceutical plants may also be fortified with lithiuim as decribed herein.

The combination of lithium with St. John's wort, a mediator of mammalian serotonin metabolism, offers a new pharmaceutical approach to the treatment of depression. The concentration of lithium in the product can be tightly controlled at the plant level. By providing lithium in a bioavailable form, the toxicity that can result from the accumulation and impaired excretion of lithium salts when administered on their own may be reduced or eliminated.

A protocol for the induction of shoot organogenesis on St. John's wort explants results in the clonal production of more than 40 de novo shoots on a 1 cm tissue segment. Masses of genetically consistent, sterile plant material were grown in a controlled environment for 2 months. Supplementation of the culture medium with lithium resulted in the significant accumulation of the mineral within 3–4 weeks as described in Example 6.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

General Procedures:

Statistical Analyses:

The design of all experiments was a complete randomized block and treatments consisted of five replications. All the experiments were repeated at least twice and the data were analyzed using SAS Version 6.12 (SAS Inc., 1995). Significant differences between means were assessed by a Student-Neuman-Keulls means separation test at $P \leq 0.05$.

Light Microscopic Studies:

The explants were harvested at weekly intervals over the 4 week incubation period and fixed immediately in formalin: acetic acid:alcohol (FAA: 5:5:90; V/V) and stored at 4° C. The tissues were dehydrated with a graded ethanol series followed by paraffin embedding. Eight $\mu$m thin sections were cut using an ultra microtome (Porter-Blum Ultra microtome MT-1, Ivan Sorvall Inc., Connecticut, USA). The sections were stained (Johnson, 1942) with alcian green and counter stained with safranine and observed under a light microscope (Zeiss, Germany).

Example 1

Micropropagation of St. John's Wort

St. John's wort seeds were sterilized by immersing in a 70% ethanol solution for 5 s, followed by an immersion in a 30% solution of 5.4% sodium hypochlorite (Lilo Products, Hamilton, Ontario) in water with one drop of Tween 20 per 500 mL for 20 min, and a three times rinse in sterile distilled water. Sterile seeds were germinated and maintained on water agar (8 $g \cdot L^{-1}$) for 16 days in darkness in a growth cabinet at 24° C. Hypocotyl sections were excised from sterile etiolated seedlings and cultured on a medium containing MS medium (Murashige and Skoog, 1962), B5 vitamins (Gamborg et al 1968), 30 $g \cdot L^{-1}$ sucrose and 3 $g \cdot L^{-1}$ gellan gum (Gelrite, Schweitzerhall Inc., South Plainfield, N.J., USA). Varying levels (0, 5, 10, 15 and 20 $\mu mol \cdot L^{-1}$) of TDZ and BAP (Sigma Chemical Co., St. Louis, USA) were incorporated into the basal culture medium in a series of experiments. Each experiment consisted of six explants per plate and 20 plates per plant growth regulator treatment. For determination of the optimal duration of exposure of the explants to the medium containing TDZ, five plates of each treatment were subcultured onto MS basal medium at days 3, 6, 9 and 12. All cultures were incubated in a growth cabinet with a 16 hour photoperiod under cool white light at 40–60 $\mu mol \cdot m^{-2} \cdot s^{-1}$. Regeneration was quantified after 18 and 23 days of culture.

Figure 2A:
FIG. 2(a) shows TDZ-induced regenerants on etiolated hypocotyl explants of St. John's wort with 10 $\mu$mol·L$^{-1}$ TDZ. Pigmentation at the tip of St. John's wort shoot primordial caused by the presence of the compound hypericin, is visible. (bar=1 mm).
Figure 2B:
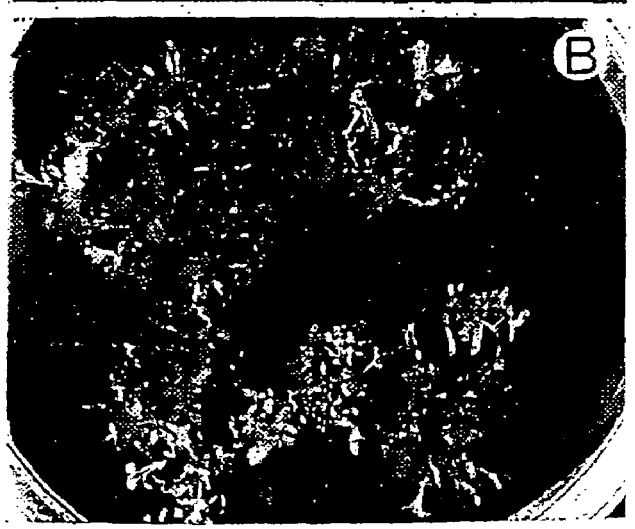
FIG. 2(b) shows the development of regenerants on hypocotyl explants after 9 days of culture on TDZ-containing induction medium and 9 days of subculture on basal medium. De novo shoots developed from all areas of the explant without an intermediate callus phase in St. John's wort. (bar=0.75 cm).
Figure 2C:
FIG. 2(c) shows sterile cultured plantlets grown from a single hypocotyl section after 2 months on basal medium in a Magenta box. (bar=1.2 cm).

Hypocotyls cultured on a medium without exogenous growth regulators produced an average of 0.8 roots/explant while rooting was not observed on explants cultured on medium containing TDZ (Table 2). De novo shoot organogenesis was induced on etiolated hypocotyl segments cultured on media supplemented with TDZ after 18–21 days (FIG. 1 (a)). Explants which remained on the TDZ medium throughout the treatment period exhibited symptoms of browning and the regenerated shoots appeared stunted and malformed as compared to those which developed on explants transferred to basal medium following a brief exposure to TDZ. Supplementation of the induction medium with TDZ alone resulted in the induction of significantly more regeneration than any other combination of growth in these experiments. Under the conditions described herein, the optimal concentration of TDZ for induction of shoot organogenesis on etiolated St. John's wort hypocotyls was 5 $\mu mol \cdot L^{-1}$. The induction of regeneration was effected by the duration of exposure to TDZ. Under the conditions defined above, the optimal culture period on TDZ-supplemented medium was 9 days with subculture onto basal media for a further 9 day period. Varying the culture conditions may change these optimal values. The protocol described herein produced a mean of 54.0 shoots/explant in 18 days (Table 2). Regenerated shoots, transferred into culture boxes containing the basal medium, formed roots and whole plantlets within 2 months (FIGS. 2(b) and (c)). Similarly, the regenerated shoots formed vigourously growing plantlets in flasks containing liquid basal medium. More than 95% of the regenerants developed into mature plantlets which were morphologically similar to seed grown plants raised in the greenhouse.

Figure 3A:
FIG. 3 shows St John's wort as produced according to the present invention.
FIG. 3b is a histological characterization showing the further development of the meristem toward the epidermis in St. John's wort hypocotyl cultured on TDZ-containing induction medium. (bar=50 $\mu$m).
FIG. 3c is a histological characterization showing the development of shoot primordia and the development of a vascular connection (arrow) in St. John's wort hypocotyl cultured for 2 weeks on TDZ-containing induction medium. (bar=166 $\mu$m).
FIG. 3d is a histological characterization showing a well developed shoot (bar=166 $\mu$m) and vascular connections between the adventitious shoot bud and the parental tissue (arrow) in St. John's wort hypocotyl cultured for 18 days on TDZ-containing induction medium. (bar=166 $\mu$m)
Figure 3B:
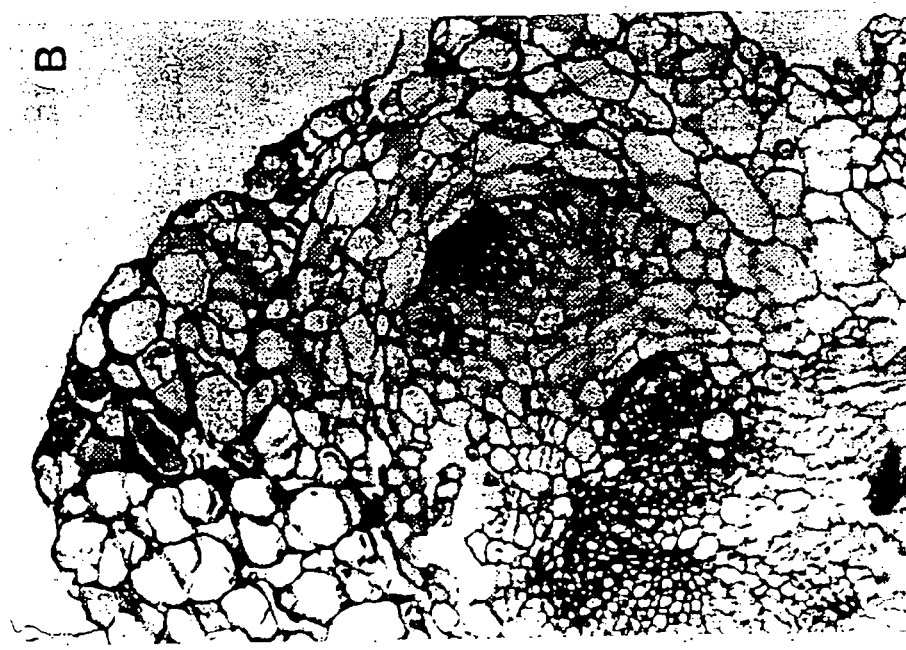
Figure 3C:
Figure 3D:
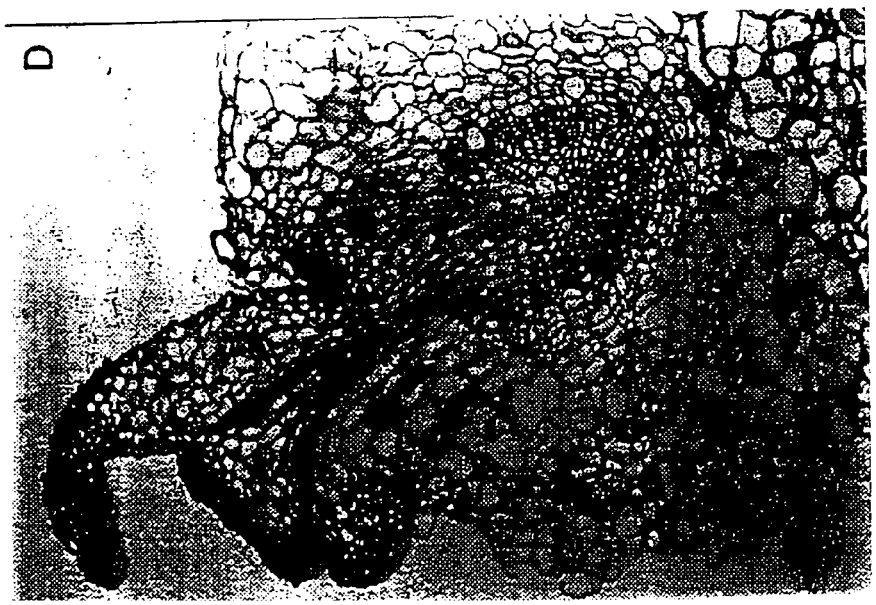
Figure 4A:
FIG. 4(a) illustrates callus formation and shoot regenerates appearing at the callus interface on petiole explants of Echinacea purpurea cultured on BAP-containing induction medium.
Figure 4B:
FIG. 4b shows individual shoot regenerants with well defined leaf initials on petiole explants of Echinacea purpurea cultured on BAP-containing induction medium after 33 days of culture.
Figure 4C:
FIG. 4c shows a late cotyledonary stage embryo on a BAP-induced petiole explant of Echinacea purpurea.
Figure 4D:
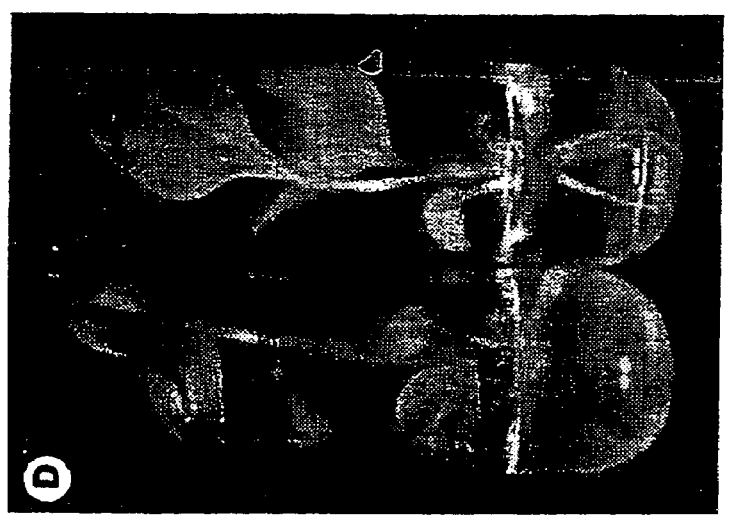
FIG. 4d shows complete plantlets grown from embryos regenerated on petioles of Echinacea purpurea cultured on BAP-containing induction medium and cultured on basal medium for 2 months.

The sections were observed under a light microscope to investigate the histological process of adventitious shoot development in St. John's wort hypocotyl cultures grown on induction medium (5 $\mu mol \cdot L^{-1}$ TDZ). Abundant meristematic zones developed at the hypodermal layers of the hypocotyl as early as 7 days after culture initiation (FIG. 3(a), arrows). The meristematic zones consisted of cells which were small in size with dense cytoplasm and a prominent nuclei (FIG. 3(a)). After 9 days of culture, these meristematic zones further differentiated and the development progressed toward the epidermis (FIG. 3(b)). In observations made after two weeks of culture, the development of shoot primordia was clearly visible (FIG. 3(c), arrows). The shoot primordia developed into fully developed shoots with vascular connections between the vascular bundle of the explant and the developing regenerant by day 18 (FIG. 3(d)).

Table 2: Effects of different concentrations of TDZ and duration of culture on TDZ supplemented medium on regeneration of St. John's wort hypocotyl explants. Statistical differences assessed by the Student Newman-Kuells mean separation test.

TABLE 2

Effects of different concentrations of TDZ and duration of culture on TDZ supplemented medium on regeneration of St. John's wort hypocotyl explants. Statistical differences assessed by the Student Newman-Kuells mean separation test.

| [TDZ] $\mu mol \cdot L^{-1}$ | Day transferred onto basal medium | Number of Shoots/hypocotyl | Number of Roots/hypocotyl |
| --- | --- | --- | --- |
| 0  | 0  | 4.6$^e$     | 0.8$^a$    |
| 5  | 6  | 27.9$^c$    | 0.3$^{bc}$ |
| 5  | 9  | 54.0$^a$    | 0.0$^c$    |
| 5  | 12 | 42.8$^{ab}$ | 0.0$^c$    |
| 10 | 3  | 11.5$^{de}$ | 0.2$^{bc}$ |
| 10 | 6  | 13.5$^{de}$ | 0.0$^c$    |
| 10 | 9  | 47.6$^{ab}$ | 0.0$^c$    |

TABLE 2-continued

Effects of different concentrations of TDZ and duration of culture on TDZ supplemented medium on regeneration of St. John's wort hypocotyl explants. Statistical differences assessed by the Student Newman-Kuells mean separation test.

| [TDZ] $\mu mol \cdot L^{-1}$ | Day transferred onto basal medium | Number of Shoots/hypocotyl | Number of Roots/hypocotyl |
|---|---|---|---|
| 10 | 12 | 46.3$^{ab}$ | 0.0$^c$ |
| 15 | 3 | 12.5$^{de}$ | 0.1$^{bc}$ |
| 15 | 6 | 22.6$^{cd}$ | 0.0$^c$ |
| 15 | 9 | 47.0$^{ab}$ | 0.0$^c$ |
| 15 | 12 | 30.2$^c$ | 0.0$^c$ |
| 20 | 3 | 20.7$^{cd}$ | 0.3$^b$ |
| 20 | 9 | 45.2$^{ab}$ | 0.0$^c$ |
| 20 | 12 | 39.0$^b$ | 0.0$^c$ |

$^{abcde}$Values within a column with different superscripts are significantly different (P < 0.05).

Example 2

Micropropagation of *Echinacea purpurea*

*Echinacea purpurea* achenes were sterilized by immersing in 70% ethanol for 30 sec, soaking in 5.4% sodium hypochloride (Javex) in water with one drop of Tween 20 per 100 ml for 18 min and rinsing three times in sterile deionized water. Due to a high amount of fungal contamination present in the seed coat of *Echinacea purpurea* achenes, PPM was included in the water agar to obtain sterile seedling germination for culture. Sterile seeds were germinated on water agar (8 g·L$^{-1}$) with 3 ml·L$^{-1}$ plant preservation mixture (PPM) in a growth cabinet in 24 hour darkness at 24° C. for 14 days. Different concentrations of PPM were included in with the water agar (1, 2, 3, 4 and 5 ml·L$^{-1}$) to determine the lowest amount which would be biostatic to fungal growth. A concentration of 3 ml·L$^{-1}$ PPM was found to be suitable for germination of *Echinacea* seeds under the present conditions as defined herein. This concentration may vary depending on the culture conditions.

Germinating seedlings were cultured onto MS medium (Murashige & Skoog, 1962) with B5 vitamins (Gamborg et al 1968), 30 g·L$^{-1}$ sucrose and 3 g·L$^{-1}$ gelrite in Magenta boxes. Petiole explants, 2 cm in length were excised from 4 week old sterile *Echinacea purpurea* plants and cultured onto induction medium comprising MS media supplemented with thidiazuron (TDZ) (0.5, 1, 5 and 10 $\mu mol \cdot L^{-1}$) or BAP (1, 2.5, 5, 7.5, 10, 12.5 and 15 $\mu mol \cdot L^{-1}$). TDZ was added to the media at concentrations of 0.5 and 1.0 $\mu mmol \cdot L^{-1}$ in combination with indole acetic acid (IAA, an auxin) at concentrations of 5 and 10 $\mu mol \cdot L^{-1}$. Explants cultured on media containing TDZ and IAA were subcultured onto MS basal media after 23 days while those cultured on media containing higher concentrations of TDZ were subcultured onto MS basal media after 4 and 8 days. All treatments consisted of 10 plates per treatment and 6 explants per plate. Treatments were incubated in a growth cabinet with a 16 hour photoperiod under cool white light at 40-60 $\mu mol \cdot m^{-2} \cdot s^{-1}$. Regeneration was quantified after 25 and 33 days for all petiole cultures and roots after 33 and 42 days of culture. The resulting regenerants were excised from petioles and subcultured onto MS basal media in test tubes for germination after 32 days of culture.

Supplementation of the culture medium with BAP as the sole growth regulating compound induced de nova shoot formation at all concentrations (FIG. 4, Table 3). In addition to regeneration, supplementation of the culture medium with BAP was also observed to induce callus formation and elongation of the petioles. When IAA was combined with TDZ or the medium was supplemented with TDZ alone, the formation of de novo regenerants was observed (Table 4).

Table 3: Effects of the cytokinin BAP on regeneration of *Echinacea purpurea* petiole explants. Statistical differences assessed by the Student Newman-Kuells mean separation test after 33 days of culture.

TABLE 3

Effects of the cytokinin BAP on regeneration of *Echinacea purpurea* petiole explants. Statistical differences assessed by the Student Newman-Kuells mean separation test after 33 days of culture.

| BAP Concentration ($\mu mol \cdot L^{-1}$) | Number of regenerants/petiole |
|---|---|
| 0 | 0.0$^c$ |
| 1 | 5.4$^{ab}$ |
| 2.5 | 8.1$^a$ |
| 5 | 6.6$^{ab}$ |
| 7.5 | 5.2$^{ab}$ |
| 10 | 3.9$^b$ |
| 12.5 | 5.2$^{ab}$ |
| 15 | 5.5$^{ab}$ |

$^{abc}$Values within a column with different superscripts are significantly different (P < 0.05).

Table 4: Effects of the auxin IAA and TDZ on production of somatic embryos and roots of *Echinacea purpurea* petiole explants. Statistical differences assessed by the Student Newman-Kuells mean separation test after 33 days of culture.

TABLE 4

Effects of the auxin IAA and TDZ on production of somatic embryos and roots of *Echinacea purpurea* petiole explants. Statistical differences assessed by the Student Newman-Kuells mean separation test after 33 days of culture.

| IAA Concentration ($\mu mol \cdot L^{-1}$) | TDZ Concentration ($\mu mol \cdot L^{-1}$) | Number of regenerants/petiole | Number of roots/petiole |
|---|---|---|---|
| 0 | 0 | 0.0$^b$ | 0.0$^b$ |
| 0 | 0.5 | 3.5$^a$ | 0.0$^b$ |
| 0 | 1.0 | 3.2$^a$ | 0.0$^b$ |
| 5 | 0 | 0.1$^b$ | 4.4$^a$ |
| 5 | 0.5 | 3.3$^a$ | 0.0$^b$ |
| 5 | 1.0 | 2.4$^a$ | 0.0$^b$ |
| 10 | 0 | 0.6$^b$ | 4.5$^a$ |
| 10 | 0.5 | 4.9$^a$ | 0.1$^b$ |
| 10 | 1.0 | 3.3$^a$ | 0.0$^b$ |

$^{ab}$Values within a column with different superscripts are significantly different (P < 0.05).

Petiole explants cultured on MS media+5 $\mu mol \, L^{-1}$ BAP were harvested at 0, 3, 5, 7, 14, 21, 28 and 35 days after culture initiation. Samples were immediately fixed in formalin/glacial acetic acid and 50% ethanol (FAA) mixture (5:5:90 v/v/v). Proper and rapid fixation of the sample was ensured by vacuuming the samples at −20 kpa for 10 min. The samples were then dehydrated through a graded tertiary butanol series and embedded in paraffin wax. Transverse 8 $\mu m$ thin sections were cut using an ultra microtome (Porter-Blum ultra microtome MT-1, Ivan Sorvall Inc., Connecticut, USA) and stained with alcian green and safranine (Jensen, 1962). The sections were observed under a compound light microscope (Zeiss, Germany).

Figure 5A:
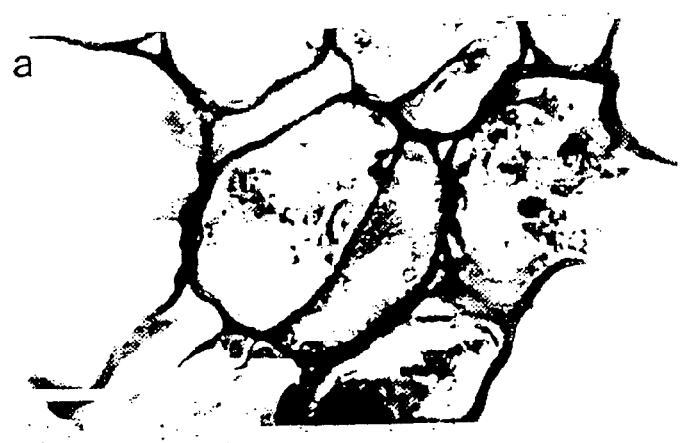
FIG. 5(a) shows a histological characterization showing periclinal cell division in the subepidermal layers of the petiole explants of Echinacea purpurea at day 3 of culturing on induction medium containing BAP. (bar=20 $\mu$m).
Figure 5B:
FIG. 5(b) shows histological characterization showing formation of promeristomatic centres (arrows) in the callus tissue of petiole explants of Echinacea purpurea at day 14 of culturing on induction medium containing BAP. (bar=680 $\mu$m).
Figure 5C:
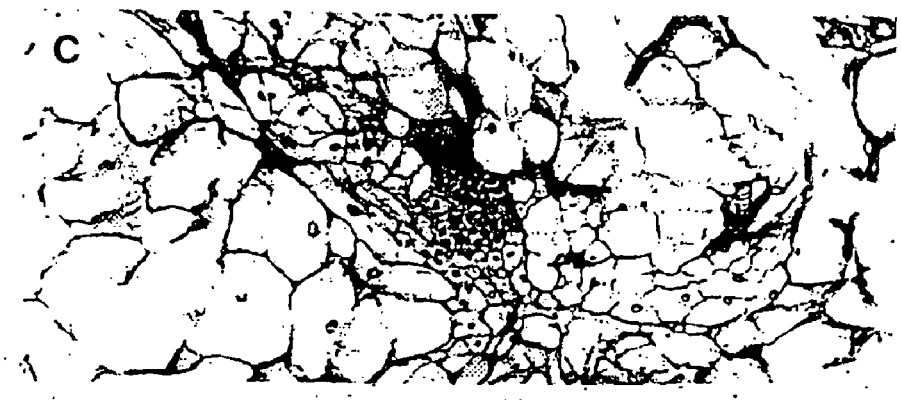
FIG. 5(c) shows histological characterization showing promeristomatic centres, having cells which were smaller in size and had a dense cytoplasm and prominent nuclei (arrows), observed on the callus tissue of the petiole explants of Echinacea purpurea by day 14 of culturing on induction medium containing BAP. (bar=50 $\mu$m).
Figure 5D:
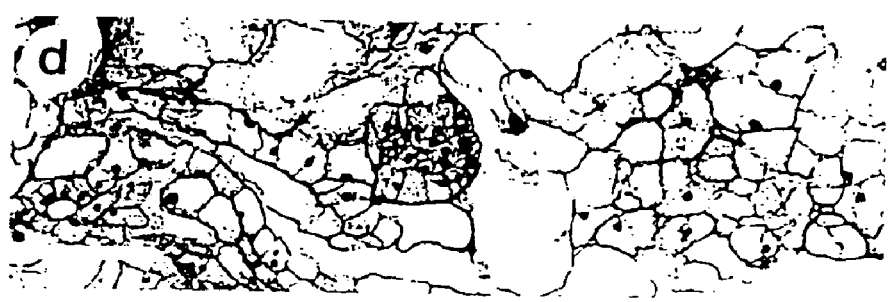
FIG. 5(d) shows histological characterization showing how the promeristomatic centres developed further to form dome shaped meristem zones which were well defined on the petiole explants of Echinacea purpurea cultured on induction medium containing BAP by day 21. (bar=50 $\mu$m).
Figure 5E:
FIG. 5(e) is a histological characterization showing development of a shoot meristem and leaf primordia on petiole explants of Echinacea purpurea after 21 days of culturing on induction medium containing BAP. (bar=320 $\mu$m).
Figure 5F:
FIG. 5(f) is a histological characterization showing a well developed shoot bud surrounded by leaf primordia formed on petiole explants of Echinacea purpurea after 28 days of culturing on induction medium containing BAP. Note that trichomes were observed to be associated with the leaf primordia and xylem elements were present at the base of the shoot bud. (bar=166 $\mu$m).

Histological observations revealed that regeneration in petiole cultures of *Echinacea* occurred primarily as a result of de novo shoot formation from callusing tissue. After 3 to 7 days in culture, the epidermal and subepidermal layers of the petiole explant started to divide (FIG. 5(a)) and formed a compact mass of callus tissue (FIG. 5(b)). This callus tissue consisted of numerous meristomatic zones (FIG. 5(a)—arrows, FIG. 5(c)). The cells of these meristematic zones were small in size with dense cytoplasm and a prominent nuclei. These meristematic zones further underwent differentiation and formed a dome shaped shoot meristem by day 21 (FIG. 5(d)—arrows). The shoot meristem developed leaf primordia (FIG. 5 (e), (f)—arrows) and eventually formed shoot buds after 21 days. A well developed shoot bud consisted of a dome shaped shoot meristem surrounded by a few leaf primordia (FIG. 5(f)). The leaf primordia had well developed trichomes. Vascular elements were observed sporadically dispersed within the callus, mainly near the base of the shoot buds (FIG. 5(f)—arrows).

Figure 6A:
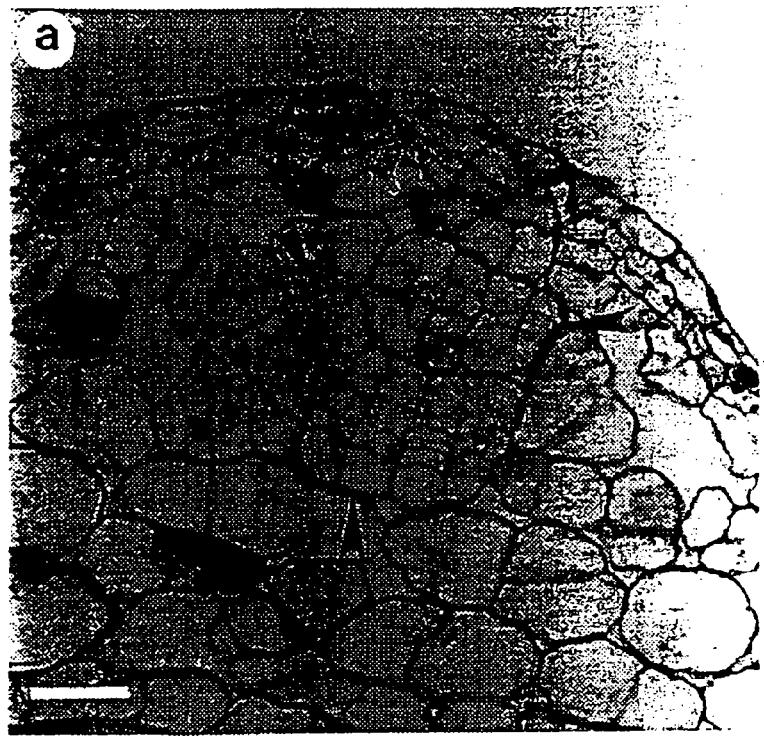
FIG. 6 shows several aspects of Echinacea as produced according to the present invention.
FIG. 6(b) is a histological characterization showing a well developed heart-shaped somatic embryo with a fully formed protoderm regenerated from petiole explants of Echinacea purpurea at 21 days of culturing on induction medium containing BAP. (bar=320 $\mu$m).
Figure 6B:
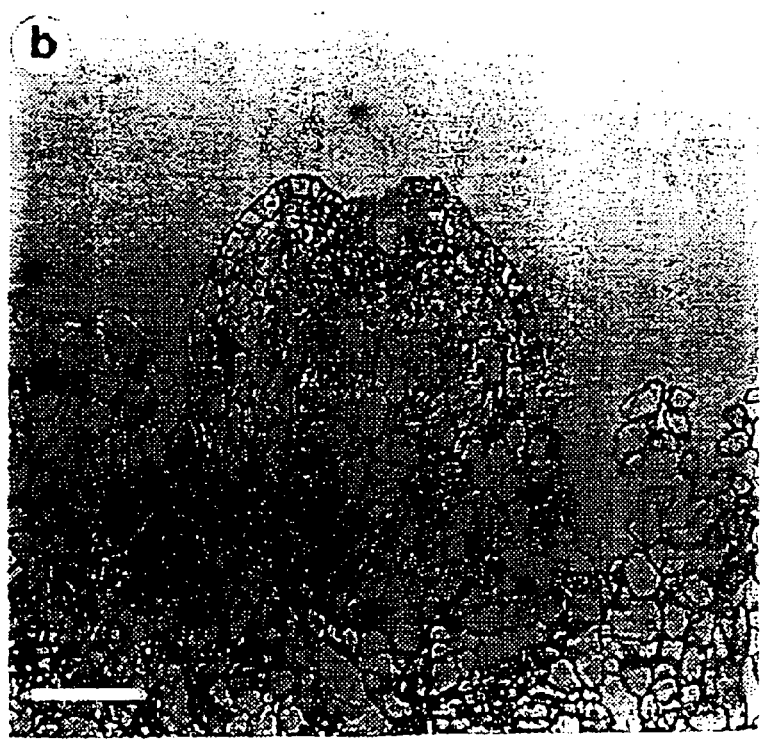

In addition to the shoot organogenesis, there was evidence of somatic embryogenesis in the histological examination of the petiole cultures. Proembryo like structures were observed in the subepidermal layers of the petiole as early as 14 days of culture (FIG. 6(a)—arrows). These proembryos appeared globular in shape, multicellular and were surrounded by a singe outer wall. The proembryos later differentiated into heart shaped somatic embryos (FIG. 6(b)). These somatic embyros may be transferred to basal medium and cultured under conditions to form plantlets.

Example 3

Micropropagation of Huang-qin

Seed Culture:

Huangqin (*Scutellaria biacalensis*) seeds were surface sterilized by dipping in 95% ethanol for 30 s, then immersing in 1.5% sodium hypochlorite containing Tween-20 (2 drops per 100 ml solution) for 18 min and then rinsed 3 times in sterile distilled water. Five seeds were cultured aseptically in each Petri dish containing 25 ml of induction medium, which consisted of MS salts (Murashige and Skoog, 1962), B5 vitamins (Gamborg et al, 1968), 30 g·L$^{-1}$ sucrose, 3 g·L$^{-1}$ gelrite and amended with various concentration of TDZ and 4 ml/l PPM (for killing fungus in seeds). The medium was adjusted to pH 5.75 before autoclaving at 121° C., 1.4 kg·cm$^{-2}$, for 20 min. The Petri dishes were sealed with Parafilm and incubated in a growth chamber at 24±2° C. with a 16 h photoperiod provided by fluorescent tubes at 30–35 μmol·m$^{-2}$·s$^{-1}$.

Huang-qin seeds began to germinate after 7 days of culture. A few seedlings regenerated shoots from crown after 10 days of culture. On day 14, all germinating seedlings on the medium with TDZ began to develop de novo shoots. The seedlings cultured on the medium with TDZ at 2.5 μmol·L$^{-1}$ had an average of 19 shoots per seedling, while the seeds germinated on the medium without TDZ had an average of 2 shoots per seedling. The medium containing 5.0, 7.5 and 10 μmol·L$^{-1}$ also showed shoot formation (Table 5).

Table 5: Effect of TDZ on Induction of Shoot Formation in Huang-qin Seedlings After 14 Days of Culture

TABLE 5

Effect of TDZ on Induction of Shoot Formation in Huang-qin Seedlings After 14 Days of Culture

| TDZ Concentration (μmol·L$^{-1}$) | Number of Shoots/Seedling |
|---|---|
| 0.0 | 2.32$^c$ |
| 2.5 | 19.85$^a$ |

TABLE 5-continued

Effect of TDZ on Induction of Shoot Formation in Huang-qin Seedlings After 14 Days of Culture

| TDZ Concentration (μmol·L$^{-1}$) | Number of Shoots/Seedling |
|---|---|
| 5.0 | 12.05$^b$ |
| 7.5 | 17.40$^{ab}$ |
| 10.0 | 17.07$^{ab}$ |
| 20.0 | 17.25$^{ab}$ | abcValues within a column with different superscripts are significantly different ($P < 0.05$).

Hypocotyl Culture:

Huang-qin seeds were sterilized as described above and aseptically cultured in Petri dishes containing 25 mL of 0.8% water agar with 4 mL/L PPM. Cultures were incubated in the dark at 24° C. for 14 days for germination. Six etiolated hypocotyl segments (about 0.5 cm) were excised from the seedlings and cultured on an induction medium comprising MS salts, B5 vitamins, 3% sucrose, 0.3% gelrite and various concentrations of TDZ (0, 2.5, 5, 7.5 and 10.0% μmol·L$^{-1}$). Cultures were incubated in a growth chamber at 24±2° C. with a 16 h photoperiod provided by fluorescent tubes at 30–35 μmmol·m$^{-2}$·s$^{-1}$ for 14 days.

Huang-qin hypocotyls on the MS basal medium in the absence of TDZ changed color to light purple after 7 days culture. After 10 days, they began to regenerate one or two adventitious shoots. After 14 and 18 days, shoot length increased quickly but no significant increase in shoot number per explant. Hypocotyls cultured on induction medium with TDZ at 2.5, 5.0, 7.5, and 10 μmol·L$^{-1}$ appeared swollen and developed a green color after 7 days of culture. After 10 days, hypocotyls in these treatments began to form shoots on the swollen tissue. The treatment with TDZ at 7.5 μmol·L$^{-1}$ induced significantly more shoots as compared with the control (Table 6). On day 14 and day 18, the number of shoots per explant on all the TDZ treatments rapidly increased. All explants on the medium containing TDZ formed shoots with an average of 8–11 shoots per explant while the explants cultured on medium containing no plant growth regulator had an average of 1 shoot per explant (Table 6).

Table 6: Effect of TDZ on Induction of Shoot Regeneration on Huang-qin Etiolated Hypocotyls

TABLE 6

Effect of TDZ on Induction of Shoot Regeneration on Huang-qin Etiolated Hypocotyls

| TDZ Concentration (μmol·L$^{-1}$) | Number of Shoots on Day 10 | Number of Shoots on Day 14 | Number of Shoots on Day 18 |
|---|---|---|---|
| 0.0 | 1.03$^b$ | 1.08$^b$ | 1.50$^b$ |
| 2.5 | 1.96$^b$ | 9.67$^a$ | 11.06$^a$ |
| 5.0 | 1.53$^b$ | 9.39$^a$ | 9.44$^a$ |
| 7.5 | 2.40$^a$ | 8.00$^a$ | 8.42$^a$ |
| 10 | 2.00$^b$ | 8.17$^a$ | 9.33$^a$ | abValues within a column with different superscripts are significantly different ($P < 0.05$).

Epicotyl Culture:

For determination of the effect of TDZ on Huang-qin epicotyl tissues, stem segments (about 1.0 cm long) from sterile seedlings grown as described above on MS basal medium for 20 days were excised and culture on induction medium. The concentrations of TDZ tested were 0, 2.5, 5.0, 7.5 10 and 20 μmol·L$^{-1}$. Induction cultures were incubated in a growth chamber at 24±2° C. with a 16 h photoperiod provided by fluorescent tubes at 30–35 μmol·m$^{-2}$·s$^{-1}$ from 14 days. In all experiments, each treatment had 5 replicates and each experiment was repeated at least twice. Regeneration of shoots was observed after 10 days, 14 days and 18 days of culture and quantified at 14 days of culture. The results for the quantification at 14 days are summarized in Table 7.

Huang-qin stems cultured on the medium containing TDZ began to swell at the edges of cuts and formed callus that appeared green in color by day 7. Regeneration of shoots was observed after 10 days of culture. On day 14, shoots had formed on all explants exposed to TDZ. The explants on the medium with TDZ had an average of 12–14 shoots per stem segment while explants cultured in the absence of growth regulators had an average of 3 shoots per explant.

Table 7: Effect of TDZ on induction of Shoot Formation in Huang-qin Stem Explants Quantified on Day 14

TABLE 7

Effect of TDZ on Induction of Shoot Formation in Huang-qin Stem Explants Quantified on Day 14

| TDZ Concentration (μmol·L$^{-1}$) | Number of Shoots/Explant |
|---|---|
| 0.0 | 3.54$^c$ |
| 2.5 | 13.61$^a$ |
| 5.0 | 14.19$^b$ |
| 7.5 | 14.58$^{ab}$ |
| 10.0 | 13.78$^{ab}$ |
| 20.0 | 12.61$^{ab}$ |

$^{abc}$Values within a column with different superscripts are significantly different (P < 0.05).

Example 4

Micropropagation of Feverfew

Preparation of the Explants:

Mature feverfew (*Tanacetum parthenium*) were used for all of the experiments. Seeds were carefully selected for uniformity and surface sterilized by immersion in 70% (v/v) ethanol for 3 min., followed by a 20 min. soak in 1.5% (v/v) sodium hypochlorite in water containing 2 drops of Tween-20 per 100 mL and 5 rinses with sterile deionized water. Sterilized seeds were individually cultured in 50 mL glass tubes containing 10 mL of water agar with 3 mL/L of PPM. Seeds were germinated in the dark at 24° C. for the first 7 days and then moved to the light (30–35 (E m$^{-2}$s$^{-1}$, 16 h photoperiod) were harvested after 2 months and cultured on a regeneration induction medium.

Regeneration Induction Medium:

Feverfew explants were cultured on an induction medium containing MS salts (Murashige and Skoog, 1962), B5 vitamins (Gamborg et al., 1965) and 30 g/L sucrose with thidiazuron (TDZ) or benzylaminopurine (BAP) at 0, 5, 10, 15, 20, 25 or 50 (mol/L. The pH of the medium was adjusted to 5.75 and 0.3% Gelrite (Scott Laboratories, Carson, USA) was included as the gelling agent prior to autoclaving at 1.4 Kg/cm$^2$ for 20 min. Regeneration was induced on stem, leaf and shoot explants cultured on an induction medium containing TDZ. The optimal level of TDZ supplementation for induction of regeneration of feverfew under the present conditions was 5 (mol/L. This value may vary depending on the conditions used.

Incubation of the Cultures:

After 1 month, regenerated shoot cultures were transferred to a basal medium containing MS salts, B5 vitamins and 3% sucrose for further development. The regenerated shoots formed roots and complete plantlets within 2 months of culture on solid basal medium. As well, prolific regeneration of plantlets was observed in cultures transferred to liquid basal medium. The optimal duration of exposure of feverfew explants to liquid basal medium was assessed in a temporary immersion bioreactor system. In this system, 30 day-old explants with prolific shoot regeneration were transferred to a sterile bioreactor flask. Cultures were incubated in the growth room at 35 μmol·m$^{-2}$·s$^{-1}$ and liquid basal medium was pumped into the flask and drained from the flask at six hour intervals. The flask environment was aerated with a constant flow of sterile air throughout the incubation period. With this protocol, massive proliferation of feverfew plantlets was achieved in a 30 day period.

Example 5

Phytofortification of *Echinacea* with Zinc

*Echinacea* achenes were sterilized by immersing in 70% ethanol for 30 sec, soaking in 5.4% sodium hypochloride (Javex) in water with one drop of Tween 20 per 100 ml for 18 min and rinsing three times in sterile deionized water. Due to a high amount of fungal contamination present in the seed coat of *Echinacea purpurea* achenes, PPM was included in the water agar to obtain sterile seedling germination for culture. Sterile seeds were germinated on water agar (8 g.L$^{-1}$) with 3 ml·L$^{-1}$ plant preservation mixture (PPM) in a growth cabinet in 24 hour darkness at 24° C. for 14 days. Different concentrations of PPM were included in with the water agar (1, 2, 3, 4 and 5 m·L$^{-1}$) to determine the lowest amount which would be biostatic to fungal growth. A concentration of 3 ml·L$^{-1}$ PPM was found to be the optimal concentration for germination of *Echinacea* seeds under the present conditions. This concentration may vary depending on the culture conditions.

Germinating seedlings were cultured onto MS medium (Murashige & Skoog, 1962) with B5 vitamins (Gamborg et al 1968), 30 g·L$^{-1}$ sucrose and 3 g·L$^{-1}$ gelrite in Magenta boxes and incubated in a controlled environment chamber for 30 days with a 16 hour photoperiod under cool white light at 40–60 μmol·m$^{-2}$·s$^{-1}$. Mature seedlings were subcultured into 125 mL flasks containing 25 mL of basal medium supplemented with zinc at 0, 50, 100, 150 or 200 mg·L$^{-1}$ and incubated in the same chamber for 30 days (liquid baslal medium, Table 1).

In experiments designed to determine the zinc uptake in micropropagated *Echinacea* plantlets, petiole explants, 2 cm in length were excised from the 4 week old sterile *Echinacea* plants and subcultured onto induction medium comprising MS media supplemented with thidiazuron (TDZ) (0.5, 1, 5 and 10 μmol·L$^{-1}$) or BAP (1, 2.5, 5, 7.5, 10, 12.5 and 15 μmol·L$^{-1}$) alone or in combination with indoleacetic acid (IAA) at concentrations of 5 and 10 μmol·L$^{-1}$. Cultures were incubated in a growth cabinet with a 16 hour photoperiod under cool white light at 40–60 μmol·m$^{-2}$·s$^{-1}$. Regeneration was quantified after 25 and 33 days for all petiole cultures and roots after 33 and 42 days of culture. The resulting regenerants were excised from petioles and subcultured into 125 mL flasks containing 25 mL of basal medium supplemented with zinc at 0, 50, 100, 150 or 200 mg·L$^{-1}$ (liquid basal media). The pH of all media was adjusted to 5.7 and experiments were conducted under controlled conditions in a growth chamber with a 16 hour photoperiod at at 40–60 $\mu mol \cdot m^{-2} \cdot s^{-1}$ for 30 days.

Plants were harvested on day 45 after treatments were initiated. Plantlets were removed with the shoot and root intact, washed with tap water, rinsed with deionized water and blotted dry with tissue paper. Fresh weight of individual plantlets was determined prior to air drying at 90° C. for 48 hours. Each sample was ground with a Waring commercial blender and mineral elements extracted with a closed Teflon vessel using the method of Topper (1990). The zinc content of the samples was determined using an AA55 Varian Atomic Absorption Spectrophotometer or by ICP Analysis. Each experiment consisted of four replicate flasks per treatment and the experiment was repeated twice.

All plants in the control, 50, 100 and 150 $mg \cdot L^{-1}$ zinc treatment groups appeared normal and healthy. At higher concentrations of zinc in the medium, some inhibition of growth was observed and the rate of plantlet growth was reduced.

Figure 7:
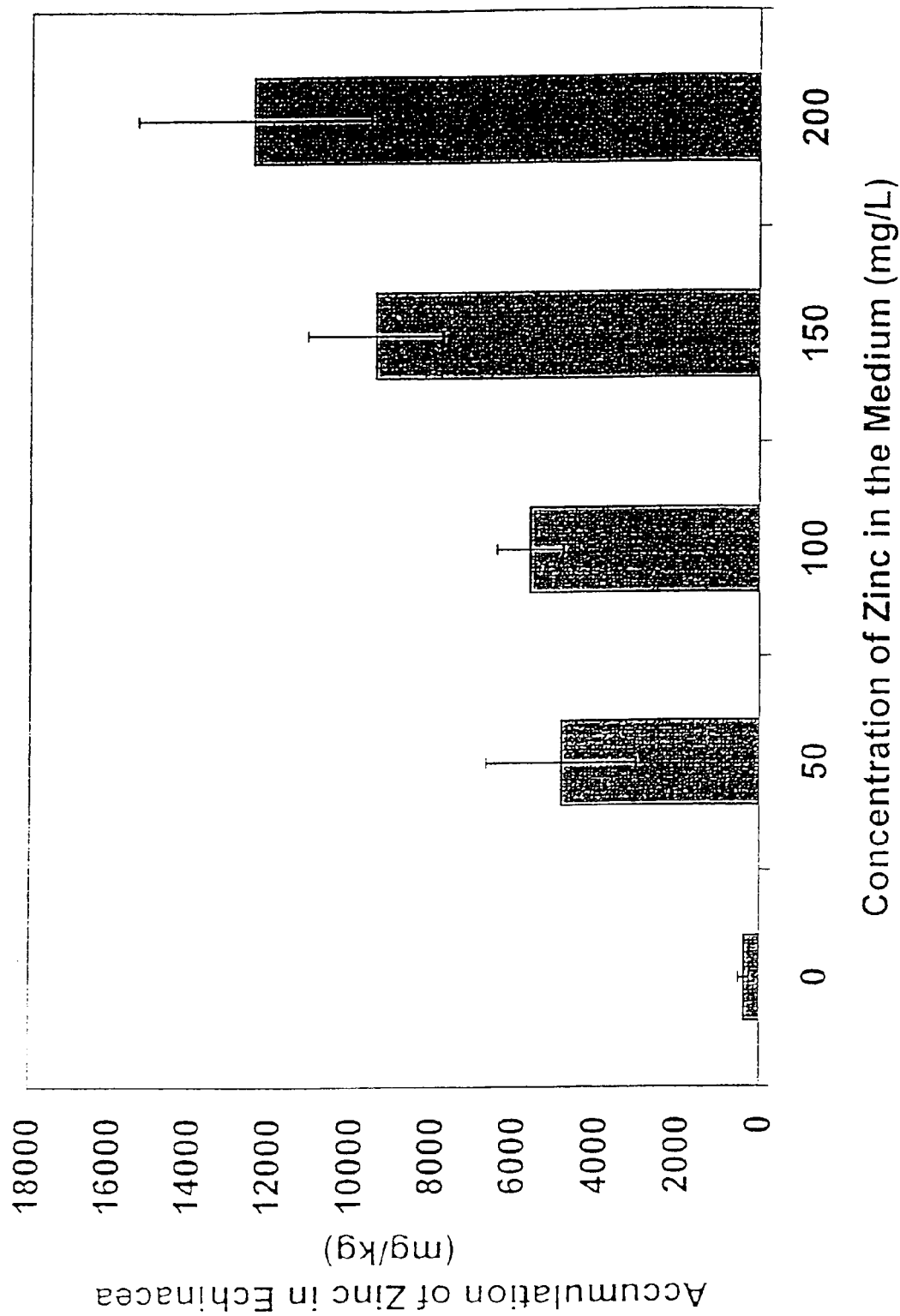
FIG. 7 shows a bar graph of the effect on zinc supplementation of the culture medium on accumulation of zinc in Echinacea plantlets after 30 days in culture.

The results, shown in FIG. 7, demonstrate that zinc accumulation increased with concentration to a maximum of 12475 mg/kg in *Echinacea* plantlets cultured on a medium supplemented with 200 $mg \cdot L^{-1}$ zinc.

Example 6

Phytofortification of St. John's Wort with Lithium

St. John's wort seedlings were obtained from sterilized seeds germinated in a controlled environment. St. John's wort seeds were sterilized by immersing in a 70% ethanol solution for 5 s, followed by an immersion in a 30% solution of 5.4% sodium hypochlorite (Lilo Products, Hamilton, Ontario) in water with one drop of Tween 20 per 500 mL for 20 min, and a three times rinse in sterile distilled water. Sterile seeds were germinated and maintained on water agar (8 $g \cdot L^{-1}$) for 16 days in darkness in a growth cabinet at 24° C. Individual seedlings were cultured in Magenta boxes on a medium containing MS medium (Murashige and Skoog, 1962), B5 vitamins (Gamborg et al 1968), 30 $g \cdot L^{-1}$ sucrose and 3 $g \cdot L^{-1}$ gellan gum (Gelrite, Schweitzerhall Inc., South Plainfield, N.J., USA). Seedling cultures were incubated in a growth cabinet with a 16 hour photoperiod under cool white light at 40–60 $\mu mol \cdot m^{-2} \cdot s^{-1}$. After 30 days, seedlings were excised from the Magenta boxes and subcultured into 125 mL flasks containing 25 mL of a basal medium containing MS medium (Murashige and Skoog, 1962), B5 vitamins (Gamborg et al 1968) and 30 $g \cdot L^{-1}$ sucrose. The medium (liquid basal medium) was supplemented with lithium at 0, 50, 100, 150 or 200 $mg \cdot L^{-1}$ and the cultures were incubated on a rotating platform with a 16 h photoperiod for 30 days at 40–60 $\mu mol \cdot m^{-2} \cdot s^{-1}$.

In a second series of experiments, the lithium accumulation of regenerated St. John's wort shoots was determined. Plantlets were regenerated as described previously. Briefly, St. John's wort seeds were surface sterilized as described above and germinated and maintained on water agar (8 $g \cdot L^{-1}$) for 16 days in darkness in a growth cabinet at 24° C. Hypocotyl sections were excised from sterile etiolated seedlings and cultured on a medium containing MS medium (Murashige and Skoog, 1962), B5 vitamins (Gamborg et al 1968), 30 $g \cdot L^{-1}$ sucrose, 5 $\mu mol \cdot L^{-1}$ of the cytokinin thidiazuron (pH was adjusted to 5.7 and 3 $g \cdot L^{-1}$ gellan gum (Gelrite, Schweitzerhall Inc., South Plainfield, N.J., USA) was added to the medium prior to autoclaving). After 9 days, the hypocotyl sections were subcultured on the same medium devoid of plant growth regulators (thidiazuron) for the development of regenerants.

All cultures were incubated in a growth cabinet with a 16 hour photoperiod under cool white light at 40–60 $\mu mol \cdot m^{-2} \cdot s^{-1}$. After 30 days of culture, explants with developing de novo shoots and sterile cultured seedlings were transferred to 125 mL flasks containing 25 mL of a basal medium containing MS medium (Murashige and Skoog, 1962), B5 vitamins (Gamborg et al 1968) and 30 $g \cdot L^{-1}$ sucrose. The medium (liquid basal medium) was supplemented with lithium at 0, 50, 100, 150 or 200 $mg \cdot L^{-1}$ lithium and the cultures were incubated on a rotating platform with a 16 h photoperiod for 30 days at 40–60 $\mu mol \cdot m^{-2} \cdot s^{-1}$. Each experiment consisted of four replicate flasks per treatment and the experiment was repeated twice.

Samples were harvested from the cultures analysed for lithium with the same protocol as described above. St. John's wort plantlets at all treatment levels appeared healthy and growth rate was unaffected by lithium supplementation of the culture medium.

Figure 8:
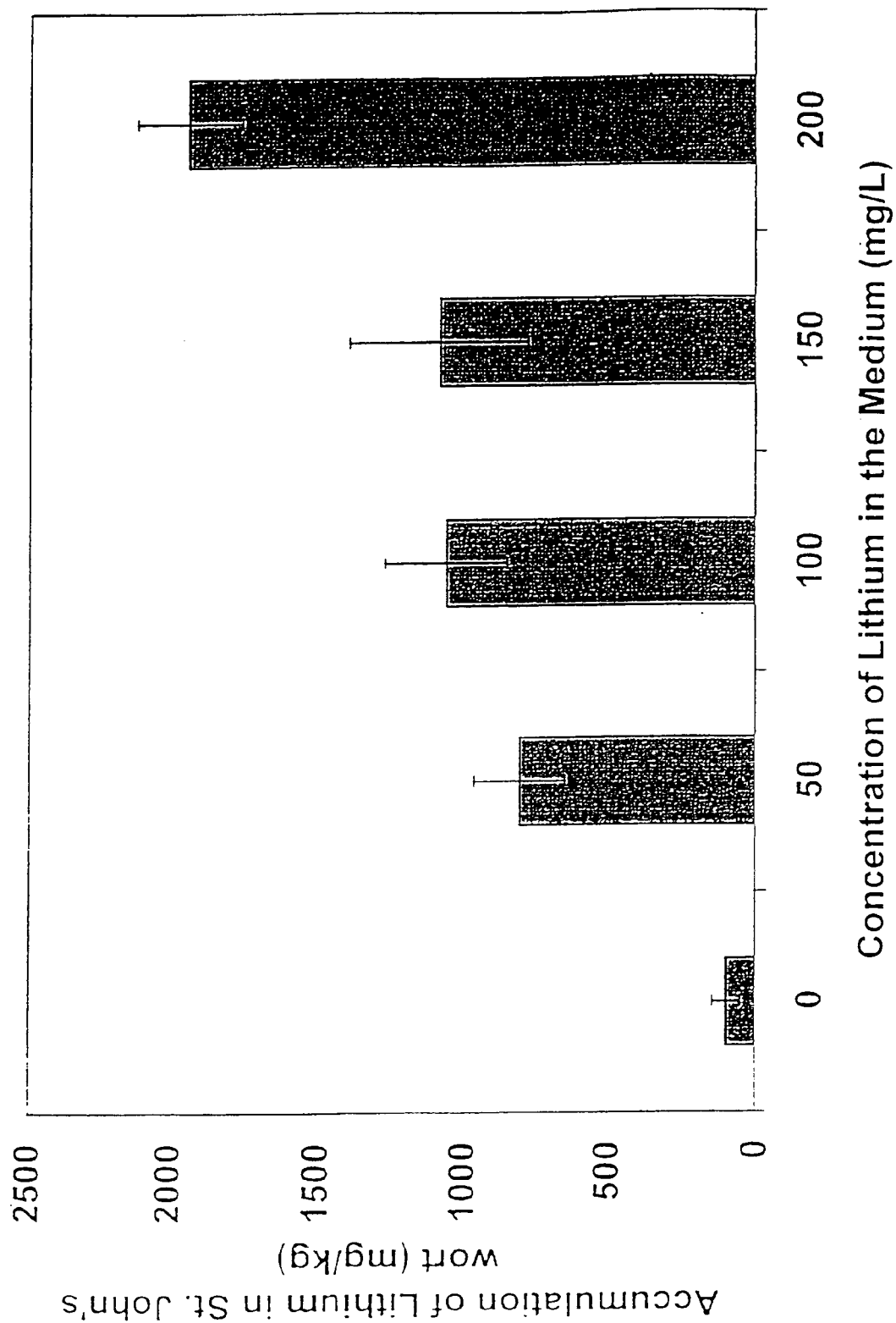
FIG. 8 is a bar graph showing accumulation of lithium in St. John's wort plantlets cultured on a medium supplemented with 0–200 mg/L lithium for 30 days.

The results, shown in FIG. 8, demonstrate that lithium accumulated to a concentration of approximately 2000 mg/kg in St. John's wort plantlets cultured on a medium supplemented with 200 $mg \cdot L^{-1}$ lithium.

The above description is not intended to limit the claimed invention in any manner, furthermore, the discussed combination of features might not be absolutely necessary for the inventive solution.

All publications, patents and patent applications are herein incorporated by reference.

REFERENCES

Betz, W. (1998) Epidemic of renal failure due to herbals. Sci. Rev. Alt. Med. 2:12–13.

Cott J M, (1997) In vitro receptor binding and enzyme inhibition by *Hypericum perforatum* extract. Pharmacopsychiat. 30 (supp.):108–112. Consumer Safety Symposium on Dietary Supplements and Herbs (1998) New Good Housekeeping Institute study finds drastic discrepancy in potencies of popular herbal supplement. Good Housekeeping Institute. New York, N.Y. Mar. 3, 1998.

Consumer Safety Symposium on Dietary Supplements and Herbs (1998) New Good Housekeeping Institute study finds drastic discrepancy in potencies of popular herbal supplement. Good Housekeeping Institute. New York, N.Y. Mar. 3, 1998.

Evans M F and Morgenstern K, (1997) St. John's wort: an herbal remedy for depression? Can. Fam. Physician. 43: 1735–1736.

Gamborg O L, Miller R A and Ojima K, (1968) Nutrient requirement of suspension cultures of soybean root cells. Exp. Cell Res. 50: 150–158.

Gibson, R. S., Yeudall, F. Drost, N. Mtitimuni, B and T. Culliman (1998) Dietary interventions to prevent zinc deficiency. Am. J. Clin. Nutr. 68:484S–487S.

Greenwald, J. 1998. Herbal healing. Time, Nov. 23, 1998. 48–58.

Hansgen K D, Vesper J and Ploch M, (1994) Multicenter double-blind study examining the antidepressant effectiveness of *Hypericum* extract LI 160. J. Geriatr. Psychiatry Neurol. 7:S15–S18.

Huetteman C A and Preece J E, (1993) Thidiazuron: A potent cytokinin for woody plant tissue culture. Plant Cell Tissue Organ Cult. 33: 105–119.

Hutchinson J M and Saxena P K, (1996) Acetylsaliscylic acid enhances and synchronizes thidiazuron-induced somatic embryogenesis in geranium (*Pelargonium×hortorum* Bailey) tissue cultures. Plant Cell Rep. 15:512–515.

Jensen, W. A. (1962) Botanical histochemistry. San Francisco: W.H. Freeman.

Johansen D A, (1940) Plant Microtechnique. McGraw-Hill Inc. New York, USA.

Kindscher, K. (1992) Medicinal wild plants of the prairie lawrence. University Press of Kansas. p. 86.

Linde K, Ramirez G and Mulrow D, (1996) St. John=s wort for depression—an overview and meta-analysis of randomized clinical trials. Br. Med. J. 313:253–261.

Lu C-Y, (1993) The use of thidiazuron in tissue culture. Cell Dev. Biol. 29: 92–96.

Miller A L, (1998) St. John's wort (*Hypericum perforatum*): Clinical effects on depression and other conditions. Altern. Med. Rev. 3:18–26.

Mok M C and Mok D W S, (1985) The metabolism of [$^{14}$C]-thidiazuron in callus cultures of *Phaseolus lunatus*. Physiol. Plant. 65: 427–432

Murashige T and Skoog F, (1962) A revised medium for rapid growth and bioassays with tobacco tissue cultures. Physiol. Plant. 15: 473–497.

Murch S J, Simmons C B and Saxena P K, (1997) Melatonin in feverfew and other medicinal plants. The Lancet. 350:1598–1599.

Murthy B N S, Murch S J and Saxena, P K, (1995) Thidiazuron-induced somatic embryogenesis in intact seedlings of peanut (*Arachis hypogaea*): Endogenous growth regulator levels and significance of cotyledons. Physiol. Planta. 94: 268–276.

Murthy B N S, Murch S J and Saxena P K, (1998) Thidiazuron: A potent regulator of in vitro plant morphogenesis. In Vitro Cell. Dev. Biol. 34:267–275.

Nahrstedt A and Butterweck L (1997) Biologically active and other chemical constituents of the herb of *Hypericum perforatum* L. Pharmacopsychiat. 30:129–134.

National Institute of Health (1997) St. John's wort study launched. Complementary and Alternative Medicine at the NIH. 4 (4):5, October, 1997.

Ruel M. T. and H. E. Bouis (1998) Plant breeding: a long-term strategy for the control of zinc deficiency in vulnerable populations. Am. J. Clin. Nutr. 68:488S–494S.

SAS Inc. (1995) The GLM procedure. In SAS/STAT Guide for Personal Computers, Version 6 (P. Stephenie ed.), pp. 183–260. SAS Institute, Inc., Cary, N. C. ISBN 0-917382-84-6.

Schardt, D. April 1998. Still out in the cold—Nutrition Action Health Letter.

Schweitzer I. And V. Tuckwell (1998) Risk of adverse events with the use of augmentation therapy for the treatment of resistant depression. Drug Saf. 19:455–464.

Sharp, W. R., Sondhal, M. R., Caldar, R. S., Maraffa, S. B. (1980) The physiology of in vitro asexual embryogenesis. Horticultural Reviews, 2:268–310.

Skoog, F. and Miller, C. O. (1957) Chemical regulation of growth and organ formation in plant tissues cultured in vitro. Symp. Soc. Exp. Biol. 11:118–140.

Sommer H and Harrer G, (1994) Placebo-controlled double blind study examining the effectiveness of an *Hypericum* preparation in 105 mildly depressed patients. J. Geriatr. Psychiatry. Neurol. 7: S9–S11.

St. John's Wort Monograph (1997) American Herbal Pharmacoepea and Theraputic Compendium HerbalGram, American Botanical Council. 40:37–45.

Visser C, Qureshi J A, Gill R and Saxena P K, (1992) Morphoregulatory role of thidiazuron: substitution of auxin and cytokinin requirement for the induction of somatic embryogenesis in geranium hypocotyl cultures. Plant Physiol. 99: 1704–1707.

Whittaker, P. (1998) Iron and zinc interactions in humans. Am. J. Clin. Nutr. 68:442S–446S.

The embodiments of the invention in which an exclusive property of privilege is claimed are defined as follows:

1. A method for the in vitro micropropagation and phytofortification of a phytopharmaceutical plant comprising:
   a) culturing a sterile explant of said phytopharmaceutical plant on an induction medium comprising at least one plant growth regulator having cytokinin activity, to form regenerated tissue;
   b) transferring said regenerated tissue to a first basal medium lacking said plant growth regulator having cytokinin activity, and culturing to form plantlets; and
   c) subculturing said plantlets onto a second basal medium supplemented with one, or more than one additive of interest at an amount from about 50 to about 200 mg/L, said additive of interest selected from the group consisting of a vitamin, boron, chromium, cobalt, copper, iron, lithium, iodine, manganese, molybdenum, nickel, selenium, silicon, tin, vanadium and zinc, to allow uptake and accumulation of said one, or more than one additive of interest in a bio-available form in said plantlet thereby producing said phytopharmaceutical plant that is phytofortified.

2. The method of claim 1, wherein after said step of culturing (step a)), and prior to said step of transferring (step b)), said regenerated tissue is placed on a basal medium and subcultured to further formation of regenerated tissue.

3. The method of claim 1 wherein after said step of transferring (step b)), said plantlet is transferred to a hydroponic environment with a recycling solution containing, said one or more than one additive of interest to allow uptake and accumulation of said one, or more than one additive of interest in a bioavailable form within said plantlet.

4. The method according to claim 1, wherein said at one plant growth regulator having cytokinin activity is selected from the group consisting of thidiazuron (N-phenyl-N'-(1,2,3-thidiazol-yl)urea), benzylaminopurine(BAP), zeatin, CPPU (N-(2-chloro-4pyridyl)-N(-phenyl urea) and 2-I-P (N-6-(2-isopentenyl) adenine).

5. The method according to claim 4, wherein said one, or more than one plant growth regulator having cytokinin activity is selected from thidiazuron (TDZ) and benzylaminopurine (BAP).

6. The method according to claim 5, wherein said induction medium comprises from about 0.001 to about 25 micromol·L$^{-1}$ of said one, or more than one plant growth regulator having cytokinin activity.

7. The method according to claim 5, wherein said sterile explant is maintained on said induction medium from about 1 to about 50 days.

8. The method according to claim 1, wherein said explant is a tissue selected from the group consisting of a seed, petiole, hypocotyl, stem, cotyledon and leaf.

9. The method according to claim 1, wherein said phytopharmaceutical plant is St. John's wort.

10. The method according to claim 9, wherein said plant growth regulator having cytokinin activity is thidiazuron.

11. The method according to claim 10, wherein the induction medium comprises thiadiazuron from about 0.001 to about 25 p.mol·L$^{-1}$.

12. The method according to claim 11, wherein the induction medium comprises thiadiazuron from about 4 to about 10 $\mu$mol·L$^{-1}$.

13. The method according to claim 9, wherein said sterile explant is maintained on said induction medium from about 1 to about 15 days.

14. The method according to claim 13, wherein said sterile explant is maintained on said induction medium from about 8 to about 10 days.

15. The method according to claim 9, wherein said explant is etiolated hypocotyl.

16. The method according to claim 1, wherein said one, or more than one additive of interest is zinc.

17. The method according to claim 1, wherein said one, or more than one additive of interest within said basal medium, is from about 0.001 to about 500 mg.L$^{-1}$.

18. The method according to claim 2, wherein, in said transferring step, said regenerated tissue is subcultured for about 1 to about 15 days.

19. A method for phytofortification of an in vitro-grown phytopharmaceutical plant comprising:
   a) culturing a sterile seedling, explant or regenerated tissues to form a plantlet; and
   b) subculturing said plantlet onto a basal medium lacking a plant growth regulator having cytokinin activity, said basal medium supplemented with one, or more than one additive of interest, at an amount from about 50 to about 200 mg/L, said additive of interest selected from the group consisting of a vitamin, boron, chromium, cobalt, copper, iron, lithium, iodine, manganese, molybdenum, nickel, selenium, silicon, tin, vanadium and zinc, to allow uptake and accumulation of said one, or more than one additive of interest in a bio-available form in said plantlet to produce a phytofortified phytopharmaceutical plant.

20. The method according to claim 19, wherein, in said step of culturing, said plantlets are produced either:
   a) on a sterile explant of said phytopharmaceutical plant grown on an induction medium comprising one, or more than one plant growth regulator having cytokinin activity, or
   b) grown from a sterile seed, or
   c) seedling in culture.

21. The method according to claim 20, wherein said at one plant growth regulator having cytokinin activity is selected from the group consisting of thidiazuron (N-phenyl-N'-(1,2,3-thidiazol-yl)urea), benzylaminopurine (BAP), zeatin, CPPU (N-(2-chloro-4pyridyl)-N(-phenyl urea) and 2-i-P (N-6-(2-isopentenyl) adenine).

22. A method for promoting shoot formation of a phytopharmaceutical plant comprising the steps of:
   a) culturing a sterile explant of said phytopharmaceutical plant on an induction medium comprising one or more plant growth regulators having cytokinin activity, to form regenerated tissue; and
   b) transferring said regenerated tissue to a basal medium lacking said plant growth regulator having cytokinin activity and culturing to form plantlets, wherein said steps of culturing and transferring result in the in vitro micropropagation involving de novo shoot formation of non-meristematic tissue of said phytopharmaceutical plant.

23. A method for the in vitro micropropagation and phytofortification of a phytopharmaceutical plant comprising:
   a) culturing a sterile explant of said phytopharmaceutical plant on an induction medium comprising one, or more than one plant growth regulator having cytokinin activity, to form regenerated tissue;
   b) transferring said regenerated tissue to a basal medium and culturing to form plantlets; and
   c) subculturing said plantlets onto a basal medium containing an additive selected from the group consisting of lithium, chromium, nickel, selenium, silicon, tin, and vanadium, to allow uptake and accumulation of said additive in a bio-available form in said plantlet, said basal medium lacking said plant growth regulator having cytokinin activity.

* * * * *